(12) United States Patent
Kartalian et al.

(10) Patent No.: US 8,882,816 B2
(45) Date of Patent: Nov. 11, 2014

(54) FIXATION AND ALIGNMENT DEVICE AND METHOD USED IN ORTHOPAEDIC SURGERY

(75) Inventors: George Kartalian, Great Falls, VA (US); Ali Siam, Stoughton, MA (US); Jordan Jacobs, Randolph, MA (US)

(73) Assignee: Proactive Orthopedics, LLC, Great Falls, VA (US)

( * ) Notice: Subject to any disclaimer, the term of this patent is extended or adjusted under 35 U.S.C. 154(b) by 110 days.

(21) Appl. No.: 13/339,904

(22) Filed: Dec. 29, 2011

(65) Prior Publication Data
US 2012/0101502 A1   Apr. 26, 2012

Related U.S. Application Data

(63) Continuation-in-part of application No. 12/184,704, filed on Aug. 1, 2008, now Pat. No. 8,696,716.

(60) Provisional application No. 60/953,657, filed on Aug. 2, 2007.

(51) Int. Cl.
| | | |
|---|---|---|
| *A61B 17/84* | (2006.01) | |
| *A61B 17/68* | (2006.01) | |
| *A61B 17/86* | (2006.01) | |
| *A61B 17/17* | (2006.01) | |

(52) U.S. Cl.
CPC ............. *A61B 17/8685* (2013.01); *A61B 17/68* (2013.01); *A61B 2017/1775* (2013.01)
USPC ............................. 606/300; 606/320; 606/328

(58) Field of Classification Search
CPC ............ A61B 17/842; A61B 2017/565; A61F 2002/4233; A61F 2002/4235
USPC ........... 606/300–302, 304, 307, 319, 320, 74, 606/323–325, 328
See application file for complete search history.

(56) References Cited

U.S. PATENT DOCUMENTS

| | | |
|---|---|---|
| 3,312,139 A | 4/1967 | Di Cristina |
| 3,469,573 A | 9/1969 | Florio |
| 4,409,974 A | 10/1983 | Freedland |
| 4,456,005 A | 6/1984 | Lichty |
| 4,688,561 A | 8/1987 | Reese |
| 4,796,612 A | 1/1989 | Reese |

(Continued)

FOREIGN PATENT DOCUMENTS

RU    2269959 C1    2/2006

OTHER PUBLICATIONS

International Search Report and Written Opinion corresponding to the PCT/US08/71961 application dated Oct. 27, 2008.

(Continued)

*Primary Examiner* — Michael T Schaper
(74) *Attorney, Agent, or Firm* — Muir Patent Consulting, PLLC

(57) ABSTRACT

Surgical anchoring systems and methods are employed for the correction of bone deformities. The anchoring system and its associated instrument may be suitable for surgical repair of hallux valgus, tarsometatarsal sprains, ankle ligament reconstruction, spring ligament repair, knee ligament reinforcement, acromioclavicular sprains, coracoclavicular sprains, elbow ligament repair, wrist and hand ligamentous stabilization or similar conditions. The anchoring system may include a fixation system for anchoring two or more sections of bone or other body parts and a system for aligning of one section relative to another section.

22 Claims, 22 Drawing Sheets

(56) References Cited

U.S. PATENT DOCUMENTS

| | | | |
|---|---|---|---|
| 4,858,601 A | 8/1989 | Glisson | |
| 5,061,137 A | 10/1991 | Gourd | |
| 5,102,276 A | 4/1992 | Gourd | |
| 5,167,664 A | 12/1992 | Hodorek | |
| 5,217,462 A | 6/1993 | Asnis | |
| 5,250,049 A | 10/1993 | Michael | |
| 5,529,075 A * | 6/1996 | Clark | 128/898 |
| 5,827,285 A | 10/1998 | Bramlet | |
| 5,908,421 A | 6/1999 | Beger | |
| 5,993,486 A | 11/1999 | Tomatsu | |
| 6,203,545 B1 | 3/2001 | Stoffella | |
| 6,283,973 B1 | 9/2001 | Hubbard et al. | |
| 6,348,053 B1 | 2/2002 | Cachia | |
| 6,458,134 B1 | 10/2002 | Songer et al. | |
| 6,464,706 B1 | 10/2002 | Winters | |
| 6,736,819 B2 | 5/2004 | Tipimeni | |
| 6,887,243 B2 | 5/2005 | Culbert | |
| 6,890,333 B2 | 5/2005 | Von Hoffmann et al. | |
| 6,908,465 B2 | 6/2005 | Von Hoffmann et al. | |
| 6,942,668 B2 | 9/2005 | Padget et al. | |
| 7,008,428 B2 | 3/2006 | Cachia et al. | |
| 7,070,601 B2 | 7/2006 | Culbert et al. | |
| 7,097,647 B2 | 8/2006 | Segler | |
| 7,112,221 B2 | 9/2006 | Harris | |
| 7,175,667 B2 | 2/2007 | Saunders et al. | |
| 7,291,175 B1 | 11/2007 | Gordon | |
| 7,326,211 B2 | 2/2008 | Padget et al. | |
| 7,625,395 B2 | 12/2009 | Muckter | |
| 7,833,227 B2 | 11/2010 | Fernandez | |
| 7,875,058 B2 | 1/2011 | Holmes, Jr. | |
| 7,951,198 B2 | 5/2011 | Sucec et al. | |
| 7,955,388 B2 | 6/2011 | Jensen et al. | |
| 8,221,455 B2 | 7/2012 | Shurnas et al. | |
| 8,277,459 B2 | 10/2012 | Sand et al. | |
| 8,398,678 B2 | 3/2013 | Baker et al. | |
| 8,425,554 B2 | 4/2013 | Denove et al. | |
| 2001/0049529 A1 | 12/2001 | Cachia et al. | |
| 2002/0198527 A1 | 12/2002 | Muckter | |
| 2003/0236555 A1 | 12/2003 | Thornes | |
| 2004/0138665 A1 | 7/2004 | Padget et al. | |
| 2004/0158253 A1 | 8/2004 | Liou | |
| 2004/0199165 A1 | 10/2004 | Culbert et al. | |
| 2004/0260297 A1 | 12/2004 | Padget et al. | |
| 2005/0177167 A1 | 8/2005 | Muckter | |
| 2005/0187555 A1 | 8/2005 | Biedermann et al. | |
| 2005/0240187 A1 | 10/2005 | Huebner et al. | |
| 2005/0281633 A1 | 12/2005 | Mercer | |
| 2006/0235410 A1 | 10/2006 | Ralph et al. | |
| 2006/0271054 A1 | 11/2006 | Sucec et al. | |
| 2006/0271055 A1 | 11/2006 | Thramann | |
| 2006/0276793 A1 | 12/2006 | Berry | |
| 2007/0162124 A1 | 7/2007 | Whittaker | |
| 2008/0172097 A1 | 7/2008 | Lerch et al. | |
| 2008/0177291 A1 | 7/2008 | Jensen et al. | |
| 2008/0208252 A1* | 8/2008 | Holmes | 606/232 |
| 2009/0036893 A1* | 2/2009 | Kartalian et al. | 606/60 |
| 2009/0131936 A1 | 5/2009 | Tipimeni et al. | |
| 2009/0210016 A1 | 8/2009 | Champagne | |
| 2009/0228049 A1 | 9/2009 | Park | |
| 2009/0264929 A1* | 10/2009 | Alamin et al. | 606/248 |
| 2010/0076504 A1 | 3/2010 | McNamara et al. | |
| 2010/0211071 A1 | 8/2010 | Lettmann et al. | |
| 2010/0249855 A1 | 9/2010 | Bless | |
| 2011/0077656 A1 | 3/2011 | Sand et al. | |
| 2011/0118780 A1 | 5/2011 | Holmes | |
| 2011/0130789 A1 | 6/2011 | Shurnas et al. | |
| 2011/0166574 A1 | 7/2011 | Hsu | |
| 2011/0224738 A1 | 9/2011 | Sucec et al. | |
| 2011/0301648 A1 | 12/2011 | Lofthouse et al. | |
| 2012/0016426 A1 | 1/2012 | Robinson | |
| 2012/0016428 A1 | 1/2012 | White et al. | |
| 2012/0071935 A1 | 3/2012 | Keith et al. | |
| 2012/0101502 A1 | 4/2012 | Kartalian et al. | |
| 2012/0191140 A1* | 7/2012 | Bonutti | 606/281 |
| 2012/0330322 A1 | 12/2012 | Sand et al. | |
| 2013/0030475 A1 | 1/2013 | Weiner et al. | |
| 2013/0030480 A1 | 1/2013 | Donate et al. | |
| 2013/0138150 A1 | 5/2013 | Baker et al. | |
| 2013/0150853 A1* | 6/2013 | Blacklidge | 606/70 |
| 2013/0158609 A1 | 6/2013 | Mikhail et al. | |
| 2013/0184708 A1 | 7/2013 | Robinson et al. | |
| 2013/0245700 A1 | 9/2013 | Choinski | |
| 2013/0245701 A1 | 9/2013 | Kartalian et al. | |

OTHER PUBLICATIONS

Foot & Ankle International, "The Arthrex, Tight Rope™ Fixation System".2007.

Timothy Charlton, M.D. "ZipTight™ Fixation System, featuring Zip Loop Technology: Ankle Syndesmosis." Surgical Protocol, Biomet Sports Medicine. Mar. 2009.

Coughlin et al. "Proximal metatarsal osteotomy and distal soft tissue reconstruction as treatment for hallux valgus deformity". Keio J Med 2005; 54 (2): 60-65. Apr. 21, 2005.

* cited by examiner

FIXATION AND ALIGNMENT DEVICE AND METHOD USED IN ORTHOPAEDIC SURGERY

CROSS-REFERENCES TO RELATED APPLICATIONS

This application is a continuation-in-part of application Ser. No. 12/184,704 filed on Aug. 1, 2008 and is related to and claims benefit under 35 U.S.C. §119(e) to provisional application Ser. No. 60/953,657, filed on Aug. 2, 2007, the disclosures of which are hereby incorporated herein by reference in their entireties.

BACKGROUND OF THE INVENTION

1. Field of the Invention

The invention relates generally to an anchoring system and an associated surgical instrument, which may have multiple uses in orthopaedic surgery such as joint stabilization, bunion correction, ligament reconstruction and similar procedures. More particularly, the anchoring system of the invention may include a system for anchoring two or more body parts together and a system for aligning movement of one anchored body parts relative to another.

2. Related Art

Various devices and methods have been used in the prior art for bone realignment, fixation of the bones or bone portions, and ligament reconstruction repair in order to correct for various orthopaedic conditions, such as hallux valgus, tarsometatarsal sprains, ankle ligament reconstruction, and spring ligament repair.

Hallux valgus is a common foot disorder of several etiologies, which can lead to significant foot pain and deformity. Hallux valgus may be defined as a static subluxation of the first metatarsophalangeal (MTP) joint with lateral deviation of the great toe and medial deviation of the first metatarsal. Moreover, the condition may be accompanied by rotational pronation of the great toe in severe cases. The skeletal deformity results in increased sensitivity to any pressure created by contact. The condition may be self-perpetuating because the pressure that the bunion creates against the patient's footwear causes the metatarsal bone at the point of contact to thicken. A direct result of the thickening of the head of the metatarsal increases the size of the resulting bunion, which increases the severity of the condition and patient discomfort associated with the condition.

One of the most common causes of hallux valgus is prolonged deformation of the foot caused by wearing shoes that do not fit properly, such as high-heeled shoes and narrowly pointed toe shoes. Here, the big toe is forced into an abnormal orientation for a long period of time, which eventually stretches out the joint capsule and promotes abnormal migration of the muscles. There are other factors that may contribute to hallux valgus, which include rounded unstable MTP joint surfaces and oblique joint surfaces located at the proximal first metatarsal joint.

The initial symptom of hallux valgus may be pain at the joint prominence when wearing certain shoes. The capsule may be tender at any stage. Later symptoms may include a painful warm, red, cystic, movable fluctuant swelling located medially and swelling and mild inflammation affecting the entire joint which is more circumferential.

The diagnosis of a hallux valgus condition may include accurately defining a number of critical measurements through the use of x-rays taken of the foot's bone structure. First, the intermetatarsal angle (IM angle) may be determined. The IM angle may be defined by the relationship of the first metatarsal shaft compared to the line of the second metatarsal shaft. Under normal conditions, the IM angle may be in the range of about 6 degrees to about 9 degrees. Secondly, the hallux valgus angle (HV angle), which may be defined by the angle of the line created at the MTP joint between the first metatarsal bone shaft and the first phalangeal bone shaft may be determined. Under normal conditions, the HV angle may be in the range of about 9 degrees to 10 degrees. The HV angle may be considered to be in the abnormal range if the measurements are greater than about 15 degrees. Finally, the condition of the MTP joint may be evaluated to determine whether there has been a lateral subluxation of the joint. The combined evaluation of these and other factors will determine the course of action to be taken.

There are numerous types of surgical procedures that may be employed to correct a bunion. Currently, the state of the art consists of various osteotomies to realign the first metatarsal (MT) and the first MTP joint. These procedures do not function through the axis of deformity. Rather, they attempt to realign the bone and joint by translating and rotating the MT through a location that is accessible and minimizes complications. However, there are several complications related to altering blood supply of the MT, and to altering the length and position of the MT associated with this surgical procedure. Furthermore, the surgical exposure required, the trauma to and shortening of the bone from sawing, and the prolonged healing time required all lead to less than satisfactory results.

One alternative to using an osteotomy to treat hallux valgus is to perform a corrective arthrodesis of the tarsometatarsal joint. The advantage of this approach is that the deformity is corrected where it is occurring, and allows for a powerful correction of large deformities. The disadvantage, however, to this approach is that a normal joint is being sacrificed, which alters the subsequent biomechanics of the foot. Additionally, the surgical technique has been found to have a high rate of complications including a high rate of not healing properly.

BRIEF SUMMARY OF THE INVENTION

The invention provides various embodiments of anchoring systems and an optional associated instrument, as well as surgical methods to optimize the surgical correction of bone deformities from a biomechanical and biological stand point, which provide numerous advantages over conventional devices and techniques currently used for joint stabilization, bunion correction or ligament reconstruction surgery and similar procedures. The invention may be implemented in a number of ways.

According to first aspects of the invention, a surgical anchor system for use in the repair of an orthopaedic condition may include one or more of a primary anchor adapted to engage a first bone, a secondary anchor adapted to engage a second bone, and a connector component extending between the primary and secondary anchors.

In embodiments, at least one of the primary anchor and the secondary anchor may be connected to the connector component in one of a plurality of positions disposed along the length of the connector component.

In embodiments, the connector component may include a ratcheting mechanism or threaded engagement. A ratcheting mechanism may include, for example, a mating engagement between an interior surface of at least one of the primary anchor and the secondary anchor and the connector component.

In embodiments, the primary anchor may be further adapted to engage the first bone by wrapping, at least partially, around the first bone and/or the secondary anchor may be further adapted to be inserted, at least partially, into the second bone. The secondary anchor may be connected to the connector component, for example, via the ratcheting mechanism or threaded engagement.

In embodiments, the secondary anchor may have a first portion disposed in a canal of the second bone and a second portion disposed against an outer surface of the second bone.

In embodiments, the first bone may be a second metatarsal and the second bone may be a first metatarsal.

In embodiments, either, or both, of the primary anchor and the secondary anchor may be adapted to engage the first metatarsal and/or the second metatarsal by wrapping, at least partially, around the metatarsal. In embodiments, either, or both, of the primary anchor and the secondary anchor may be contoured to an anatomical shape of a bone to be treated, such as the first or second metatarsal, a phalanx, etc. Such contours may include, for example, developable and/or non-developable surfaces. As used herein, developable surfaces are those with zero Gaussian curvature, e.g. generalized cylinders, cones, etc., whereas non-developable surfaces include Gaussian curvature, e.g. partial spheroids, three-dimensional saddles, depressions, etc. In embodiments, a preformed contour of at least one of the primary anchor and the secondary anchor may include a saddle, or depression, that substantially matches an anatomical shape of the first or second metatarsal.

In embodiments, either, or both, of the primary anchor and the secondary anchor may include a base, configured to extend axially along a length of a bone to be treated, and one or more flanges attached to the base and extending generally transversely to the base. In embodiments, the base may be configured to extend axially along a length of a metatarsal and the flanges may include a dorsal portion, and/or a plantar portion, configured to wrap over, or under, the metatarsal, respectively.

In embodiments, either, or both, of the primary anchor and the secondary anchor may be adapted to be secured to a plurality of connectors, e.g. secured to two connectors disposed diagonally, crossing or parallel to one another. In embodiments, either, or both, of the primary anchor and the secondary anchor may include a plurality of perforations for receiving the connector(s). In embodiments, one or more perforations of the primary or secondary anchor may be threaded for fixedly, or adjustably, securing the connector(s) to the primary or secondary anchor.

In embodiments, either, or both, of the primary anchor and the secondary anchor may be an implantable anchor adapted to be inserted and secured in a bone canal. The implantable anchor(s) may include outer threads for securing the anchor in the bone canal. The implantable anchor(s) may also include one or more threaded sockets or perforations for fixedly or adjustably securing the connector(s) to the primary or secondary anchor.

In embodiments, at least one of the primary anchor and the secondary anchor may be bioabsorable and fabricated from a material selected from the group consisting of polylactic acid, bone allograft, and hydroxyapatite coral.

In embodiments, at least one of the primary anchor and the secondary anchor may be non-bioabsorbable and fabricated from a material selected from the group consisting of stainless steel and titanium.

In embodiments, at least one of the primary anchor and the secondary anchor may be osteogenic and coated with a bone growth factor.

In embodiments, the connector component may be fabricated from a material selected from the group consisting human dermis, porcine intestinal mucosa, porcine intestinal mucosa, fetal bovine skin, porcine skin, cadeveric fascia, polytetrafluorethylene, polypropylene, marlex mesh, absorbable suture, non-absorable suture, and umbilical tape.

In embodiments, the connector component may be fixedly attached to at least one of the primary anchor and the secondary anchor in at least one direction, or fixedly attached to at least one of the primary and secondary anchor in two directions.

In embodiments, the connector component may be pivotally attached to at least one the primary anchor and the secondary anchor.

In embodiments, the connector component may function to secure a reduction between the HV angle of the first metatarsal and a proximal phalanx.

In embodiments, the primary anchor and/or the secondary anchor may be adapted to engage the respective bone by wrapping, at least partially, around the respective bone, and the primary anchor and/or the secondary anchor may be adapted to connect to the connector component along the length of the connector component.

In embodiments, the primary anchor and/or the secondary anchor may be adapted to connect to the connector component in variable positions along the length of the connector component.

In embodiments, the connector component may include a spacer adapted to connect to the anchors in a predetermined fixed position.

In embodiments, the primary anchor and/or the secondary anchor may include a flexible loop through which at least part of the connector component may be passed. In embodiments, the connector component may include a flexible portion and may be configured as a unitary construction with the flexible loop.

According to further aspects of the invention, a surgical method for repair of hallux valgus may include one or more steps of: entering the tissues of the foot affected with hallux valgus by performing at least one incision; performing a soft-tissue release to release the abductor tendon, fibular sesamoid attachments and the lateral metatarsalphalangeal (MTP) joint capsule; shaving the exostosis; securing a primary anchor to a second metatarsal; securing a secondary anchor to a first metatarsal; and/or connecting the primary and secondary anchors to one another by a connecting component. In embodiments, the primary anchor and/or the secondary anchor may be secured to the respective metatarsal by wrapping the anchor, at least partially, around the respective metatarsal.

In embodiments, the at least one incision may include one of i) a medial incision at the first metatarsal; ii) a lateral incision to the second metatarsal at its distal portion; and iii) a first web space incision.

Embodiments may include one or more further steps of: creating a tunnel across the second metatarsal; placing the primary anchor at least partially around the second metatarsal; inserting the connector component through the primary anchor and the tunnel; securing the connector component to an outer surface of the primary anchor; and/or securing the connector component to the secondary anchor.

In embodiments, the step of securing the connector component to an outer surface of the primary anchor may include attaching a clip to a portion of the connector component that substantially prevents the connector component from pulling back through the primary anchor.

In embodiments, the step of securing the connector component to the secondary anchor may include adjustably engaging a portion of the connector component with an interior surface of the secondary anchor.

In embodiments, the step of securing the connector component to the secondary anchor may include adjustably engaging a threaded portion of the connector component with a threaded interior surface of the secondary anchor.

In embodiments, the primary anchor may include at least one suture receiving portion. Embodiments may include a step of suturing at least one of a tendon, ligament, and a plantar plate to the suture receiving portion.

In embodiments, the primary anchor and the connector component may be integrally formed and/or the primary anchor may include a loop and a free end. Embodiments may include one or more steps of wrapping at least part of the integrally formed primary anchor and connector component around the second metatarsal; feeding the free end through the loop; feeding the free end through the first metatarsal; and/or removing an excess portion of the free end that extends through the first metatarsal.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification; illustrate embodiments of the invention and together with the detailed description serve to explain the principles of the invention. No attempt is made to show structural details of the invention in more detail than may be necessary for a fundamental understanding of the invention and various ways in which it may be practiced.

DETAILED DESCRIPTION OF THE INVENTION

Figure 1:
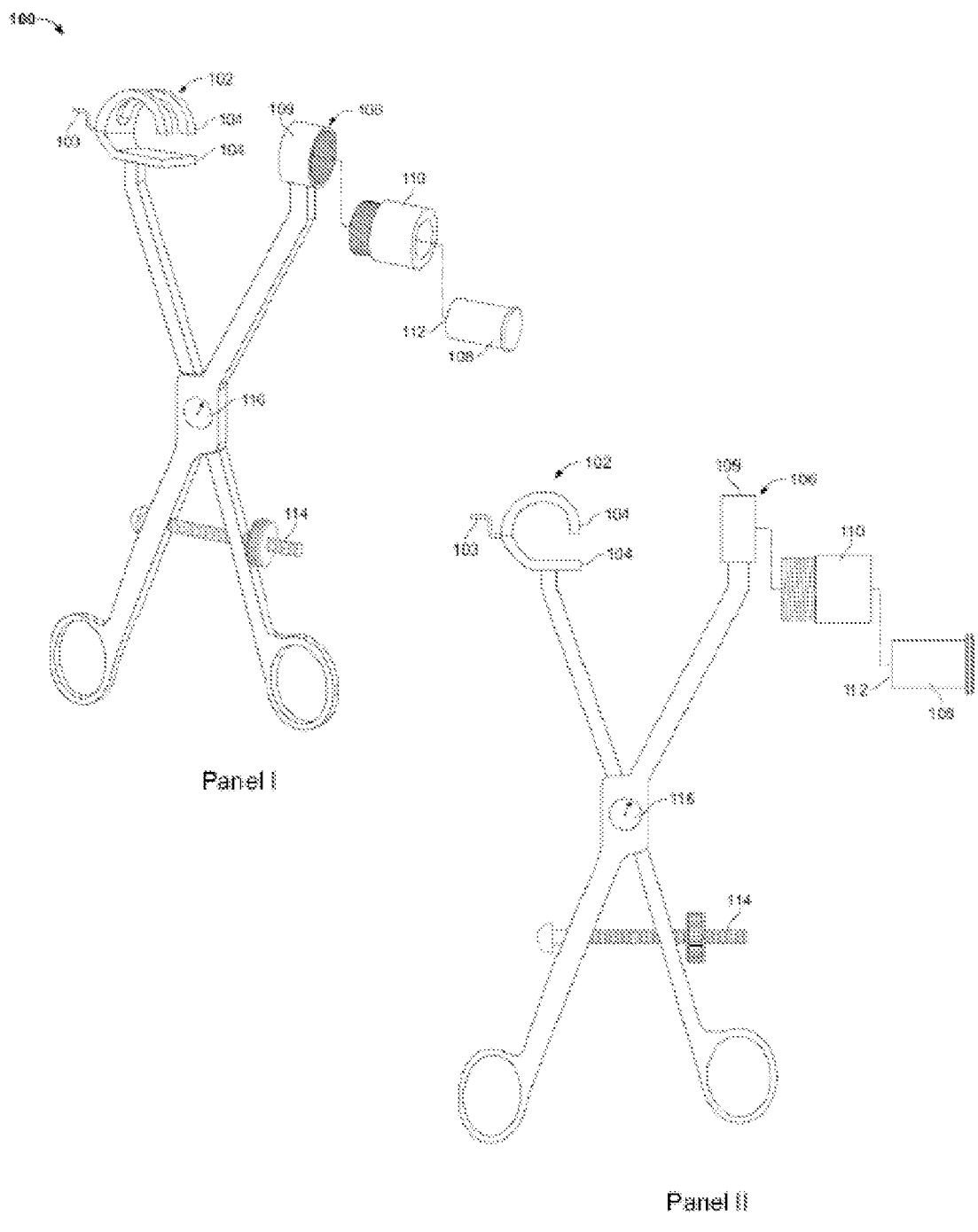
FIG. 1 is a schematic showing one embodiment of a surgical instrument constructed according to principles of the invention, which instrument may be employed to insert an anchoring system of the invention or similar device. Panel I is a side view of the surgical instrument constructed to principles of the invention and Panel II is a front view of the surgical instrument constructed to principles of the invention.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. It also is to be noted that as used herein and in the appended claims, the singular forms "a," "an," and "the" include the plural reference unless the context clearly dictates otherwise. Thus, for example, a reference to "an anchor" is a reference to one or more anchors and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein.

Any numerical values recited herein include all values from the lower value to the upper value in increments of one unit provided that there is a separation of at least two units between any lower value and any higher value. As an example, if it is stated that the concentration of a component or value of a process variable such as, for example, size, angle size, pressure, time and the like, is, for example, from 1 to 90, specifically from 20 to 80, more specifically from 30 to 70, it is intended that values such as 15 to 85, 22 to 68, 43 to 51, 30 to 32 etc., are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Moreover, provided immediately below is a "Definition" section, where certain terms related to the invention are defined specifically. Particular methods, devices, and materials are described, although any methods and materials similar or equivalent to those described herein can be used in the practice or testing of the invention. All references referred to herein are incorporated by reference herein in their entirety.

BMP is bone morphogenetic protein
bFGF is basic fibroblast growth factor
GAMs are gene-activated matrices
IM is the intermetatarsal angle
HV is the hallux valgus angle
MT is metatarsal
MTP joint is metatarsophalangeal joint
PLA is polylactic acid The term "intermetatarsal angle" or "IM angle," as used herein generally refers to the angle that may be measured between the line of the first and second metatarsal shafts. In the normal foot, the IM angle is in the range of about 6 degrees to about 9 degrees. In a patient afflicted with hallux valgus, the IM angle is about 15 degrees.

The term "hallux valgus angle" or "HV angle," as used herein generally refers to the angle that may be measured between the line of the first metatarsal shaft and the proximal phalanx. In the normal foot, the HV angle is in the range of about 9 degrees to about 10 degrees. In a patient afflicted with hallux valgus, the HV angle is about 30 degrees.

The terms "active agent," "drug," "therapeutic agent," and "pharmacologically active agent" are used interchangeably herein to refer to a chemical material or compound which, when administered to an organism (human or animal) induces a desired pharmacologic effect. Included are derivatives and analogs of those compounds or classes of compounds specifically mentioned that also induce the desired pharmacologic effect. In particular, the therapeutic agent may encompass a single biological or abiological chemical compound, or a combination of biological and abiological compounds that may be required to cause a desirable therapeutic effect.

By the terms "effective amount" or "therapeutically effective amount" of an agent as provided herein are meant a nontoxic but sufficient amount of the agent to provide the desired therapeutic effect. The exact amount required will vary from subject to subject, depending on the age, weight, and general condition of the subject, the severity of the condition being treated, the judgment of the clinician, and the like. Thus, it is not possible to specify an exact "effective amount." However, an appropriate "effective" amount in any individual case may be determined by one of ordinary skill in the art using only routine experimentation.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, the present method of "treating" individuals afflicted with hallux valgus, as the term "treating" is used herein, encompasses treatment of hallux valgus in a clinically symptomatic individual.

The terms "condition," "disease" and "disorder" are used interchangeably herein as referring to a physiological state that can be detected, prevented or treated by the surgical techniques, devices and/or therapeutic agent as described herein. Exemplary diseases and conditions in which the anchoring system, methods, and therapeutic agents of the invention may be used may include, but are not limited to, hallux valgus, Lis-Franc injury, midfoot sprains, flat feet, acromiocavicular sprains, coracoclavicular sprains, tarsal-metatarsal sprains, or similar conditions.

The term "patient" as in treatment of "a patient" refers to a mammalian individual afflicted with or prone to a condition, disease or disorder as specified herein, and includes both humans and animals.

The term "biomaterial," as used herein generally refers any suitable natural, synthetic material, absorbable, non-absorbable, or recombinant material such as extracellular matrix bioscaffolds, cadaveric fascia, suture-type materials, or umbilical tape that may be used as part of the anchoring system of the invention. As the skilled artisan will recognize, biomaterial may be flexible and/or elastic, or more rigid, dependent on usage.

The term "bioabsorbable" as used herein generally may include a bioabsorbale material such as poly-D, L-lactic acid, polyethylene glycol, polydioxanone, polylactic acid, 70L/30DL polylactide, polyglycolide, poly(orthoester), calcium sodium metaphosphate, hydroxyapatite, calcium phosphate, polytetra fluoroethylene, collagen I, II, IX, X, and XI, durapatite, and hydrogel.

The terms "polymer" or "biopolymer," as used herein generally refer to a compound having two or more monomer units, and is intended to include linear and branched polymers, and copolymers, the term "branched polymers" encompassing simple branched structures as well as hyperbranched and dendritic polymers. The term "monomer" is used herein to refer to compounds that are not polymeric. "Polymers" or "biopolymers" herein may be naturally occurring, chemically modified, or chemically synthesized.

The term "cortex" as used herein, generally refers the outer wall of a bone.

The anchoring system of the invention may have multiple uses in orthropaedic surgery. In particular, the invention may be used in a surgical procedure for insertion of the anchoring system and an associated surgical instrument to facilitate proper insertion of the anchoring system. The anchoring system of the invention may include a system for aligning two or more body parts, such as sections of bone, ligaments, tendons, tissues, and the like, and a system for fixing one section of relative to another section. As such, the anchoring system, including the fixation system and an alignment system may be made of any biocompatible material, and specifically, a bioabsorbable material. Alignment may refer to any change in position along various geometric axes (X, Y and Z) in isolation or in concert. More particularly, the anchoring system and its associated instrument may be suitable for surgical repair of hallux valgus, tarsometatarsal sprains, ankle ligament reconstruction, spring ligament repair, knee ligament reinforcement, acromioclavicular sprains, coracoclavicular sprains, elbow ligament repair, wrist and hand ligamentous stabilization, and similar conditions.

Referring to FIG. 1, a surgical instrument 100 is illustrated that may be employed for insertion of an anchor device of the invention suitable for the alignment and stabilization of the target bone(s). Instrument 100 may be fabricated from stainless steel, titanium, or any other material or combinations of material to produce an instrument that is relatively hard, impervious to damage by accidental contact with a drill bit, non-corrosive, and biocompatible. Instrument 100 may have a first end 102 and a second end 106, which are shown from different perspectives to better illustrate their features. End 102 may function as a caliper, which may be configured as a towel clip or configured to include two vertically spaced plates 104 that may function to center instrument 100 on the desired bone, such as a metatarsal. Thus, one of the plates may be curved or other shape to conform to the parts being clamped, and include two prongs as shown in FIG. 1. The plates may be spring biased towards each other by any means known in the art. Moreover, once the plates have been placed around the bone, the position of the plates may be secured by a locking mechanism 103, which may fix the relative positions of the plates by any conventional means.

Alternatively, the first arm 102 of the instrument 100 may use a cerclage wire around the metatarsal instead of the plates 104. Once the wire is passed around the metatarsal, each limb of the wire may be passed through cannulated guides on the second arm 102. The more distal, or lateral, guide may be a part of a curved plate that may rest along the plantar and lateral surface of the metatarsal. The more medial limb of the wire may pass through an adjustable guide that may slide down to the dorsal surface of the metatarsal and lock in place. This locking mechanism may provide secure fixation while centralizing the distal arm 102 along the second metatarsal regardless of variations in width.

The second end 106 may be configured as a cannulated sleeve 108 to function as a drill guide. Specifically, sleeve 108 may have an outer sleeve 110 and an inner sleeve 112. The sleeve 108 may be removably attached to ring 109 by a connection with its outer sleeve 110, such as by threads for engaging complementary threads on ring 109. The outer sleeve 110 may be attached to ring 109 by any other known mechanical connection such as interference fit, and the like. The instrument 100 may act as reduction forceps to align two bones or reduce the distance between the bones, as desired.

Moreover, instrument 100 may allow for correction of any rotational deformity (pronation) when used for surgical correction of a bunion.

In a further embodiment, instrument 100 may include a locking clamp 114 to hold the instrument 100 in position once the final alignment of the bones has been achieved. The locking clamp may be fabricated and configured as understood by those skilled in the art. Furthermore, instrument 100 may include an automatic angle indicator 116 to provide the surgeon with an estimate of the angle between the bones requiring correction. Specifically, one skilled in the art appreciates that trigonometry may be used to estimate the angle between the two bones using known data regarding the length of the bones from x-rays or from anthropomorphic averages along with the final distance between the instrument arm 118 and instrument arm 120 to estimate the angle. The instrument 100 then may be suitably calibrated to show the angle between the bones.

In one embodiment, the anchoring system of the invention and an associated instrument for insertion of the anchoring system may be employed for surgical repair of hallux valgus or bunion correction. The surgical correction may involve a soft-tissue release, placement of instrument 100 on the first metatarsal and the second metatarsal to properly insert an anchoring and alignment system of the invention, properly aligning and securing the reduction of the IM angle of the first metatarsal, and subsequent removal of instrument 100, as described immediately below.

The surgical repair of hallux valgus may commence with a medial incision at the first metatarsal and an incision lateral to the second metatarsal at its distal portion followed by a web space soft-tissue release through a small dorsal incision, followed by placement of instrument 100. Specifically, the distal soft tissue procedure may involve release of the adductor hallucis and the flexor hallucis brevis as they are elevated from the lateral sesamoid and released from their attachment to the fibular side of the first proximal phalanx. The soft-tissue release may result in release of the adductor tendon, fibular sesamoid attachments, and the lateral MTP joint capsule, which aids in correction of the bones and placement of the surgical instrument 100. This is followed by a Silver bunionectomy to shave the exostosis, which results in further release of the medial soft tissue. Next, the surgical instrument 100 may be placed to the targeted location, which may be on two separate bones or across a joint requiring correction.

After the instrument 100 is placed on the bones and the bone is set in the desired orientation, the reduction or realignment may occur to the desired angle as estimated by the angle indicator 116. For example, first end 102 may be placed on the distal second bone (second metatarsal) and second end 106 may be placed on the proximal first bone (first metatarsal). The sleeve 108 on the proximal end of instrument 100 may be used as a drill guide. Initially, a first sleeve 108 having an inner diameter 112 in the range of about 3 millimeters (mm) to about 4 mm, which is capable of accommodating a large diameter drill, may be used as a guide to create a tunnel across the proximal first bone in line with the end 102. Subsequently, sleeve 108 is removed and replaced with a new sleeve 108 having a smaller inner diameter 112 in the range of about 1 mm to about 2 mm. The new sleeve 108 may then serve as a guide for a smaller diameter drill to make a pilot hole in the distal second bone.

Figure 2:
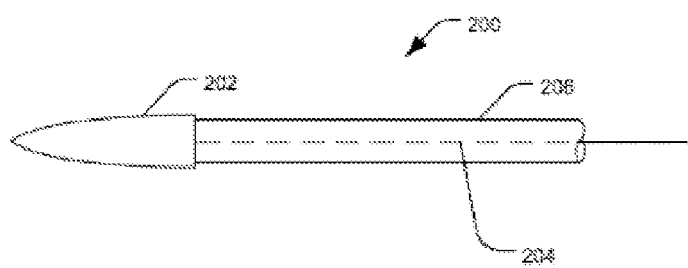
FIG. 2 is a schematic illustrating one embodiment of an anchoring system constructed according to principles of the invention.

In a further embodiment, a small anchor as depicted in FIG. 2 is set in the pilot hole created in the distal second bone. Referring to FIG. 2, anchor 200 includes an anchor region 202 and a connector region 204. The anchor region 202 may be capable of functioning as an intramedullary fixation device, a suspension fixation device, a drill and screw type fixation device or the like. If the anchor region 202 is an intramedullary type, it may have two arms that release in opposite directions within the bone canal to gain secure purchase. Alternatively, the anchor region 202 may be of a specific geometric shape that allows one-way passage through the cortical drill hole, but will subsequently become rigidly fixed within the bone canal once it passes through the cortex of the bone. The anchor region 202 may be non-absorbable and/or osteogenic and may be fabricated from, but not limited to stainless steel, titanium, and other suitable materials. Additionally, the anchor region 202 may be absorbable and/or osteogenic and may be fabricated from, but not limited to, polylactic acid, bone allograft, and hydroxyapatite coral.

In yet a further embodiment, the connector region 204, which is placed across the first and second metatarsals and functions to secure the reduction of the IM angle, may be fabricated from any suitable biocompatible material (biomaterial) and may be surrounded by a hollow sleeve 206. For example, the biomaterial may include any natural or synthetic materials such as Graff Jacket® (Wright Medical Technology), human dermis, Restore® (Depuy Orthopaedics), porcine intestinal mucosa, Cuffpath® (Arthrotek), porcine intestinal mucosa, TissueMend® (TEI Biosciences), fetal bovine skin, Permacol® (Tissue Science Laboratories), porcine skin, cadeveric fascia, polytetrafluoroethylene, polypropylene, marlex mesh, Ethibond®, FiberWire® (Mitek), any other absorbable and/or non-absorbable sutures, Arthrex®, and umbilical tape. The biomaterial may be flexible and/or elastic, or more rigid, dependent on usage. The biomaterial 204 in communication with the anchor may be either tubular or flat. The length, shape, geometry and thickness of the biomaterial may be dependent upon usage. Moreover, hollow sleeve 206 may provide rigidity for placement if the anchor is passed through the first proximal bone and into the second distal bone. Further, the hollow sleeve 206 may be absorbable and may be fabricated out of, but not limited to, polylactic acid, bone allograft, and hydroxyapatite coral. After the anchor 200 is secured within the second bone, the hollow sleeve 206 may be removed and the biomaterial passed through the hole in the first proximal bone.

Figure 3:
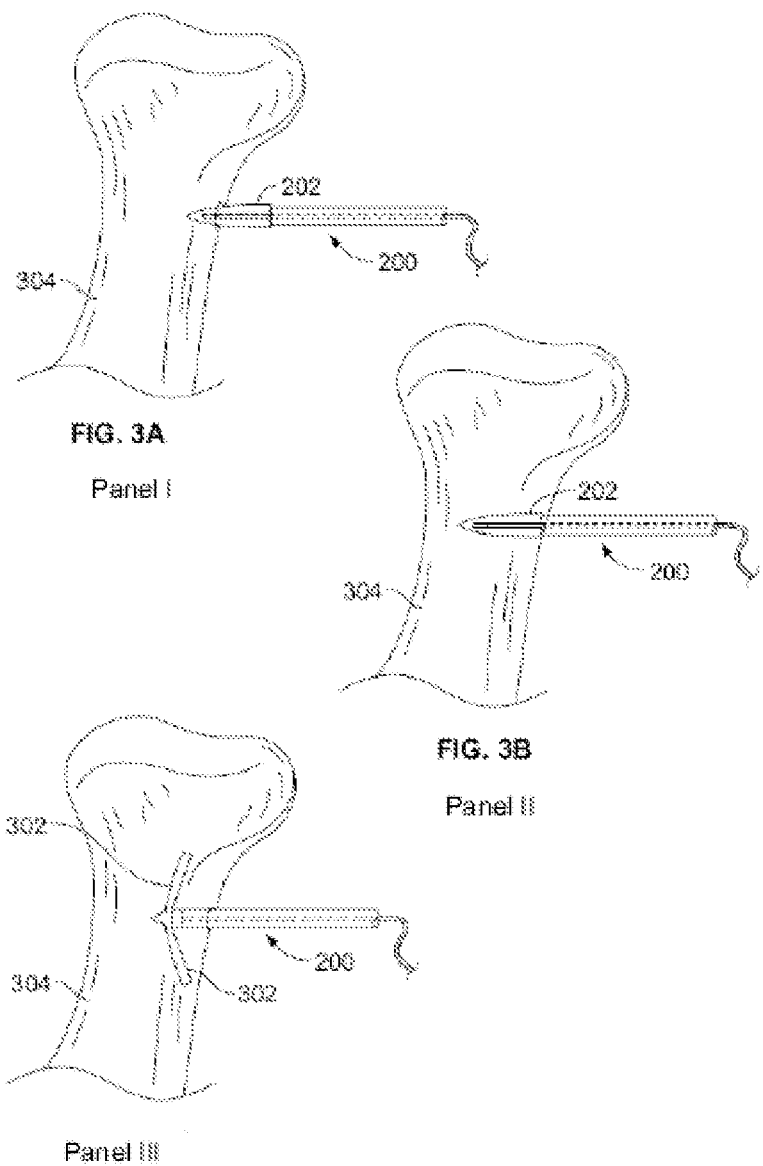
FIGS. 3A and 3B schematically show insertion of the anchoring system of the invention into the canal of the target bone. Panel I shows the anchoring system as it passes through the cortex of the bone. Panel II shows insertion of the anchoring system into the canal of the bone. Panel III shows the anchoring system securing itself within bone canal. In Panel III, the arms of the anchoring system are released in opposite directions to secure the system, according to principles of the invention.

FIG. 3 schematically shows the progression of setting an anchor 200 in the pilot hole created in the distal second bone. As shown in FIG. 3, the anchor region 202 is similar to an intramedullary fixation device having two arms 302 that release outwardly in opposite directions within the bone canal 304 to secure the anchor 200 in place. The arms 302 may be pushed out of the sleeve 206 mechanically, be formed of thermally activated materials such as nitinol, or expanded by any other means known in the art. As described further below, embodiments of the invention may include inserting a connector component through a bore in the distal second bone, such as in the vicinity of anchor region 202. When the connector component extends completely through the bone, it may be secured, for example, by an anchor that wraps at least partially around the bone, as shown, e.g., in FIG. 10.

Figure 4:
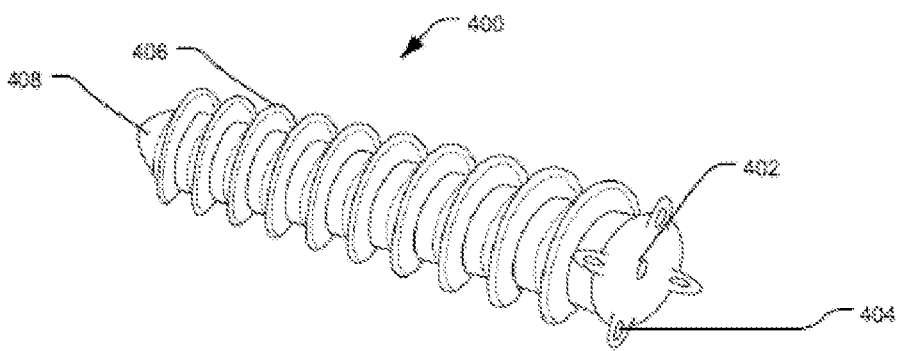
FIG. 4 is a schematic showing one embodiment of an interference screw constructed according to principles of the invention.

In yet a further embodiment, an interference screw may be inserted in the tunnel created in the proximal first bone after anchor 200 is properly engaged in the bone canal of the second distal bone. Turning to FIG. 4, an interference screw 400 is depicted having a throughbore 402 and a plurality of loops 404 or other attachment devices configured to allow a suture to pass through. Additionally, the screw 400 may be externally threaded 406 to engage the bone of the canal. Specifically, screw 400 may be threaded along its length and the threads may stop near its tip 408. As the biomaterial 204 is held at the desired length and tension, the screw may be inserted into the hole in the first proximal bone and may be advanced until a secure interference fit is achieved. The biomaterial 204 may be threaded through loops 404 to secure the repair. Once the screw 400 is set within the canal of the bone, instrument 100 may then be removed. After removal of the instrument 100, soft tissue repair may be initiated by tightening the capsular tissue to a fixed point into the attachment sites 404 of the screw 400. If the screw 400 is tightened further, tension and rotational correction may be achieved and the biomaterial 204 may be achieved to reinforce the repair, thereby resulting in a more secure repair.

Figure 5:
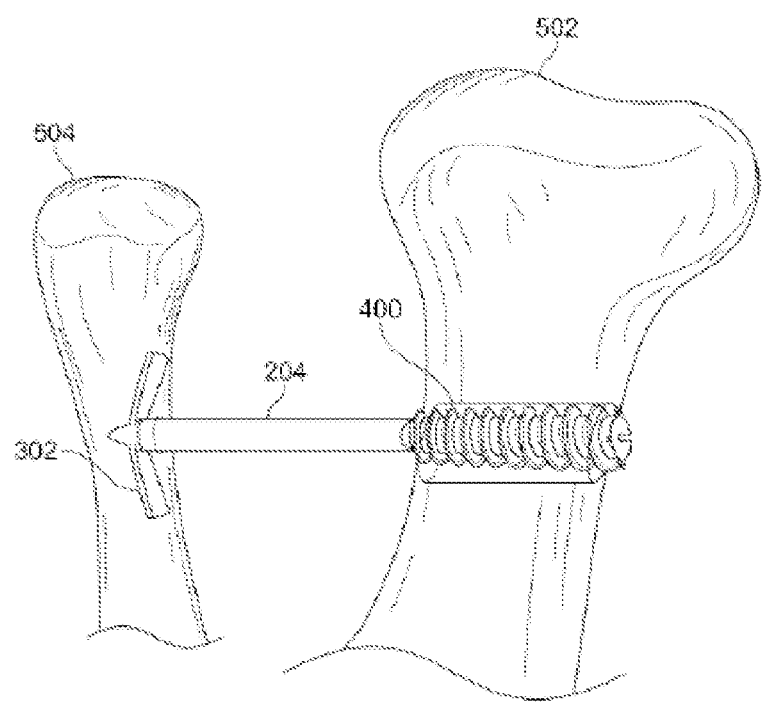
FIG. 5 is a schematic showing the final configuration of the anchoring system of the invention employed for surgical correction of hallux valgus.

Turning to FIG. 5, another configuration of the anchoring system is schematically shown after a surgical bunion repair, according to principles of the invention such as described above. Here, a proximal first bone 502, a distal second bone 504, anchor region 202, connector region 204, and interference screw 400 are shown. The anchor region 202 with its two expanded arms 302 is embedded within the canal of bone 504, and the connector region 204 extends from the distal second bone 504 and threaded through the through-bore of the interference screw 400 embedded in the proximal first bone 502. As mentioned above, embodiments of the invention may also include the distal second bone 504 being tunneled with a through bore, which may have an anchor wrapped at least partially around the bone. In such embodiments, the connector component may not be secured inside the distal second bone 504, but secured, instead, to an outer surface of the wrap around anchor at one or more positions.

In an alternate embodiment of the invention, the instrument 100 and anchor device 200 may be used to correct or repair other orthopaedic conditions, such as mid-foot or tarsometatarsal sprains. The instrument 100 may achieve and may maintain a reduction along the path of the ruptured ligament. After the smaller anchor 200 is set in the second metatarsal, the biomaterial 204 may be used to reconstruct the Lis Franc ligament with the remaining biomaterial 204 secured within the first bone such as the medial cuneiform. The instrument 100 may have the second distal arm centered around the proximal second metatarsal and the first or proximal arm may be placed on the medial cuneiform. Instrument 100 may then assist in performing the reduction of the Lis Franc joint. A drill sleeve 108 with a larger diameter may then be used on the proximal arm to create a tunnel through the medial cuneiform. The drill sleeves with the larger diameter is removed and replaced with a drill sleeve having a smaller diameter. Next, a small pilot hole may be made in the base of the second metatarsal. The anchor 200 may be set into the pilot hole of the second metatarsal and the biocompatible material 204 may be pulled through the medial cuneiform along the anatomic path of the Lis Franc ligament. The biomaterial 204 may then be secured in the medial cuneiform with the interference screw 400.

Figure 6:
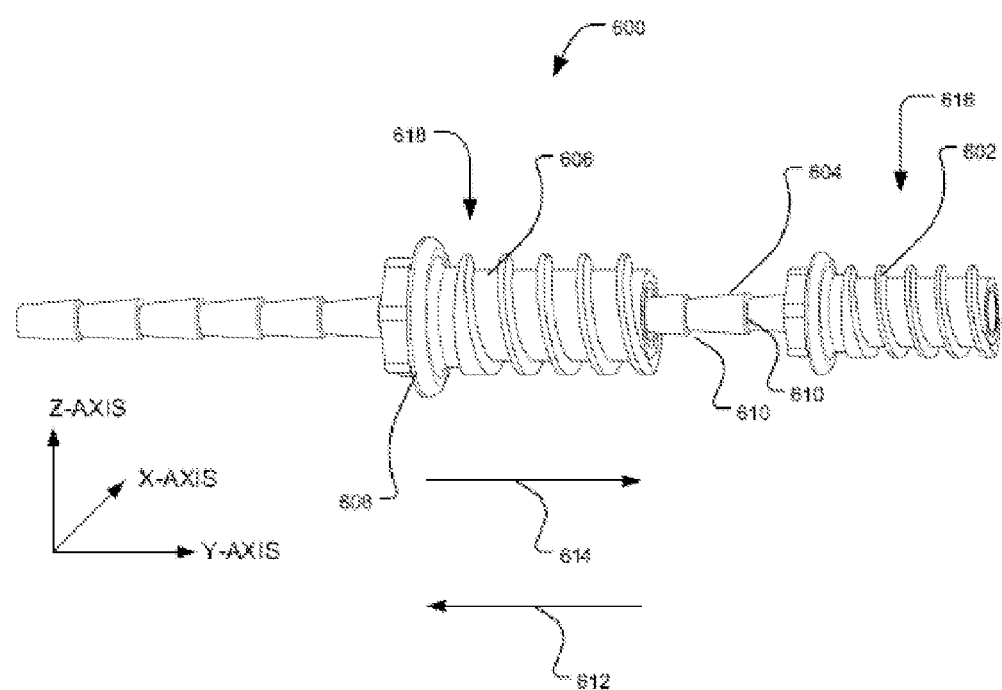
FIG. 6 is a schematic showing one embodiment of the anchoring system of the invention having screw threads as the anchoring mechanism for both the primary and secondary anchors for positioning the anchors relative to each other and a ratcheting mechanism.
Figure 7:
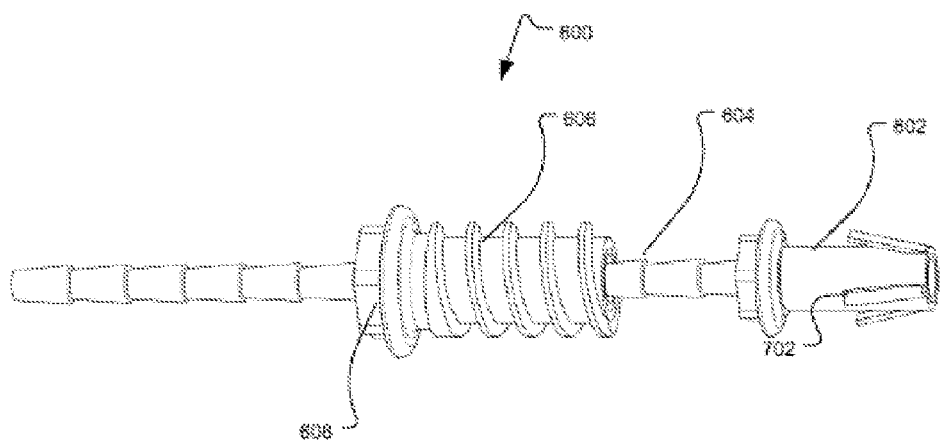
FIG. 7 is a schematic showing one embodiment of the anchoring system of the invention having an expandable material as the locking mechanism of the primary anchor.
Figure 8:
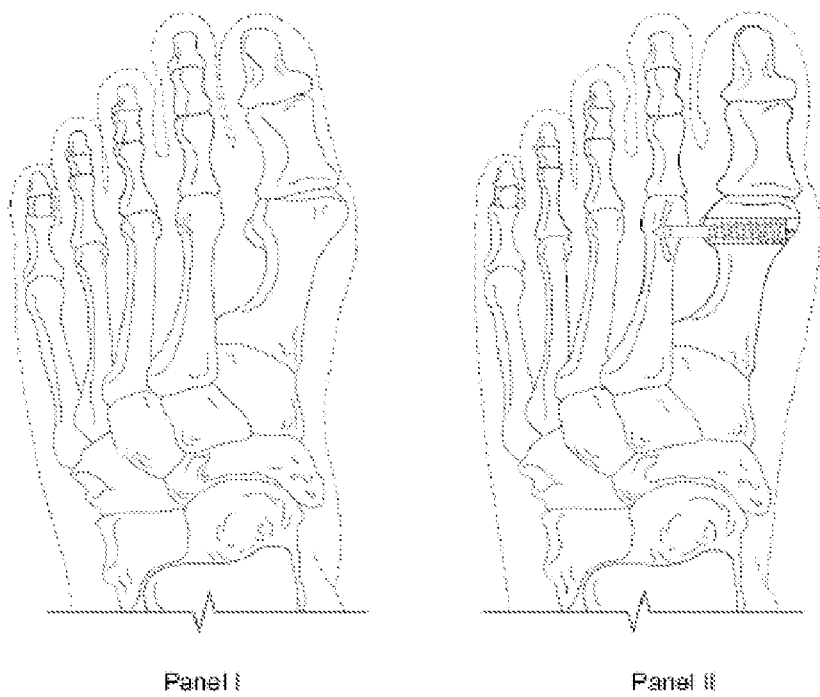
FIG. 8 is a schematic showing a final configuration of the anchoring system FIG. 7 employed for surgical correction of hallux valgus. Panel I shows hallux valgus of the joint of the first metatarsal. Panel II shows correction of hallux valgus of the first metatarsal after correction using the anchoring system of FIG. 7.

According to yet further embodiments of the invention, the anchoring systems illustrated in FIGS. 6-8 may be used for anchoring and stabilizing the first metatarsal via fixation to the second metatarsal. In these embodiments, at least one of the anchors may be disposed on and locked in place on the connector component via a one-way or two-way ratcheting mechanism, a threaded engagement mechanism, and the like, to achieve precise positioning, as described in more detail below. In FIG. 6, an anchoring system 600 having a distal portion 616, a proximal portion 618, a primary anchor 602, a connector component 604, a proximal secondary anchor 606, and a flange 608 is shown. Anchoring system 600 may be employed using the methods along with device 100, as described above, for fixating the relative position first metatarsal to the second metatarsal and thereby reducing the IM angle of the first metatarsal. The primary anchor 602 and/or the secondary anchor 606 may be bio-absorbable for short-term use or bioactive for long-term tissue integration and/or may also be coated to reduce the potential for infection or to promote tissue in-growth, as described below.

In embodiments, the connector component 604 and secondary anchor 606 may provide for precise relative positioning and locking of the secondary anchor in a number of positions along the axial length of the connector component via a one-way ratcheting locking mechanism, a threaded engagement mechanism, or the like. For example, the outer surface of connector component 604 may have a plurality of spaced protrusions 610, such as angular teeth, ridges, barbs, detents, ribs, threads, or the like, which are adapted to be retained in a mating surface provided on the inside surface of the secondary anchor 606. The mating connectors may function to resist motion of the connector component 604 in at least one direction. The locking action formed by the mating connection may act, for example, as a one-way ratcheting mechanism. As shown in FIG. 6, the mating connections may be forward facing to facilitate motion of the connector component 604 in one direction 614 while resisting movement of the connector component 604 in a opposite direction 612. Thus, connector component 604 or may have fixed stops precut into the connector component 604 for the secondary anchor 606 to lock against. The ratcheting mechanism thus functions similar to a "cable tie," where a locking component slides over the connector component, adjusting its finished length. In addition, the arrangement of the mating connections may be reversed so the projections may be disposed on the inner surface of the secondary anchor and matingly received in the connector component. Other one-way or two-way locking mechanisms may also be employed such as Velcro type connections or other suitable fabrics.

The position of the secondary anchor 606 may be adjusted by pulling on the connector component to move the component 604 relative to anchor 606 and secure it in place via the locking/ratcheting mechanism. This adjustment could also be accomplished by a variety of mechanical means including winding the connector component onto a screw or using a lever for tension. The ratcheting may be automatic or may be actuated by the user. The ratcheting may be permanent or allow for future adjustment. Thus, the locking device may take the form of a releasable, two-way ratcheting mechanism known in the art. Regardless, the invention should not be construed to be limited to any particular locking or ratcheting mechanism, as these types of mechanisms are well known in the art and can be readily made by techniques known to those of ordinary skill in the art. As described herein, adjustment means for modifying a distance between anchors, or a connector length, may include ratcheted, barbed, threaded, winding, and/or clipped mechanisms, or other mechanisms known to those of ordinary skill in the art.

The connector component 604 of system 600 may be composed of suture material that may be elastic, braided, or monofilament in nature, or may be a wire, a polymeric strap, or any other suitable ratcheting material. The connector component 604 may be attached directly to one or both anchors or may be attached by an intermediate mechanism. The connection may be asymmetric to provide greater stiffness or flexibility in one direction over another.

The primary anchor 602 and the secondary anchor 606 may be composed of a single body and may be secured into the second metatarsal and first metatarsal, respectively, using such means as screw threads (as shown in FIG. 6), barbs, loops/cuffs, and the like to result in an interference fit. In an alternate embodiment, primary anchor 602 and/or secondary anchor 606 may be composed of a material that expands to lock the anchor in place. For example, FIG. 7 shows system 600 with primary anchor 602 having material 702, connector component 604, and secondary anchor 606. Subsequent to insertion of primary anchor 602 into the second metatarsal, material 702 expands to secure primary anchor 602 in the bone canal of the second metatarsal. FIG. 8 is a schematic illustrating a final configuration of the anchoring system of FIG. 7 (Panel II) for the correction of hallux valgus of the first metatarsal as shown in FIG. 8, Panel I.

Figure 9:
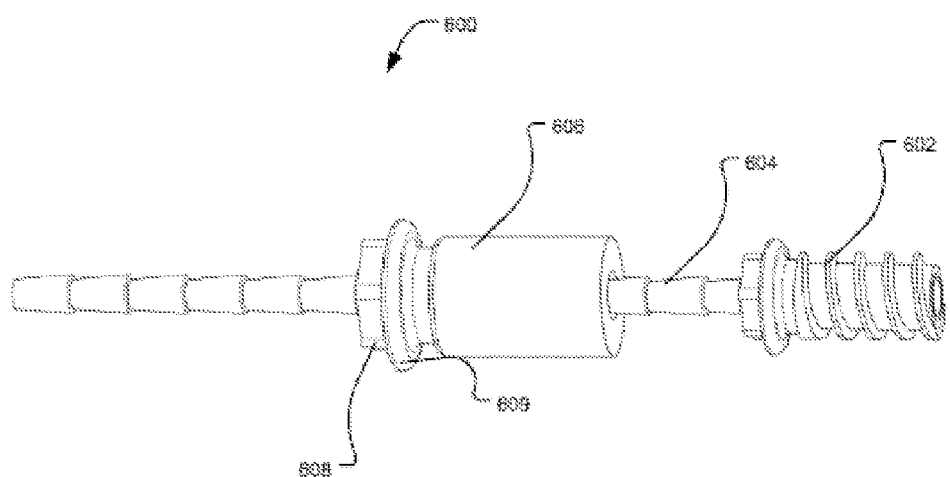
FIG. 9 is a schematic showing one embodiment of the anchoring system of the invention in which the secondary anchor includes a bushing portion disposed inside a bone canal and a flange disposed against the outside of the bone.

FIG. 9 illustrates yet another embodiment of the invention where the secondary anchor 606 is adapted to have a slideable fit within the first metatarsal and/or has an outer dimension that the allows the secondary anchor to act as a bushing to take up the space drilled in the first metatarsal or other bone. For example, secondary anchor 606 may have a smooth outer surface like a washer or a bushing having dimensions selected to slide within the hole drilled in the first metatarsal. The secondary anchor 606 has a flange 608 with a surface 609, which abuts the proximal side of the first metatarsal thereby "sandwiching" the first metatarsal between the secondary anchor 606 and the primary anchor 602 fixed within the bone canal of the second metatarsal.

Alternatively, primary anchor 602 and/or secondary anchor 606 may be connected a linkage to allow for a greater range of motion of the anchoring system, such as a ball joint and/or formed from a somewhat flexible material. In other words, if the axial motion of the anchoring system is along the y-axis of connector component 604, the linkage would permit motion along the x- or z-axis or a combination of x- and z-axes. For example, a ball joint or another type of lost-motion connection may be used to connect the primary anchor 602 and the connector component 604 and/or the connector component and the secondary anchor. This enables the relative position of the metatarsal to be adjusted in all three dimensions.

Figure 10:
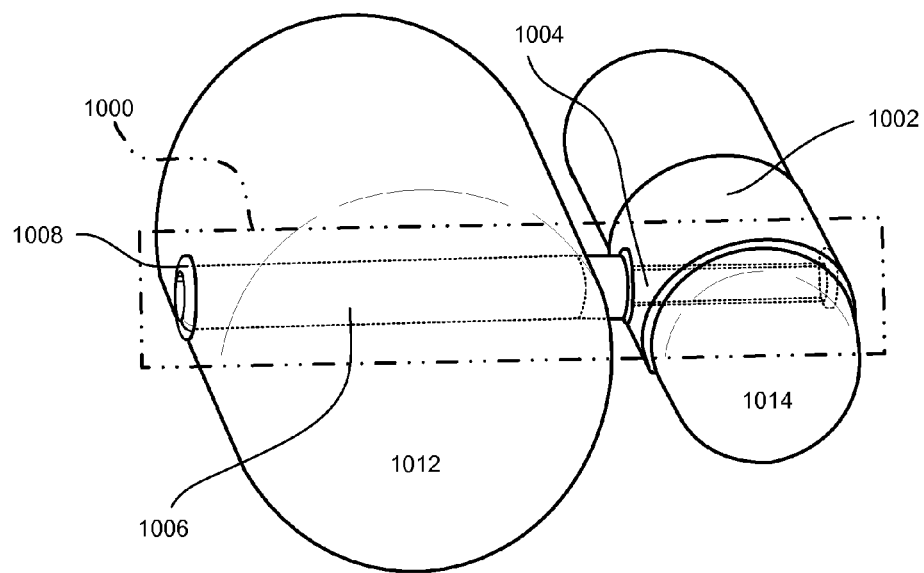
FIG. 10 is a schematic showing one embodiment of the anchoring system of the invention in which the primary anchor includes a ring-shaped anchor disposed around the outside of the bone.

According to yet further embodiments of the invention, the anchoring systems illustrated in FIGS. 10-14 may be used for anchoring and stabilizing the first metatarsal and the second metatarsal, or other bones, together. In these embodiments, at least one of the anchors may be wrapped at least partially around a bone. In the embodiments of FIGS. 10-13, one of the anchors may be secured to the connector component in a variety of adjustable positions, for example, via a one-way or two-way ratcheting mechanism, a threaded engagement mechanism, or the like, to a desired positioning. In FIG. 10, an anchoring system 1000 having a primary wrap-around anchor 1002, a connector component 1004, and a proximal secondary anchor 1006, with a flange 1008 is shown. Anchoring system 1000 may be employed using the methods along with instrument 100, as described above, for fixing the relative position of a first bone, such as a first metatarsal 1012, to a second bone, such as a second metatarsal 1014, and thereby reducing, for example, an IM angle of a first metatarsal. The primary anchor 1002 and/or the secondary anchor 1006 may be bio-absorbable for short-term use or bioactive for long-term tissue integration and/or may also be coated to reduce the potential for infection or to promote tissue in-growth, as described below.

Figure 11:
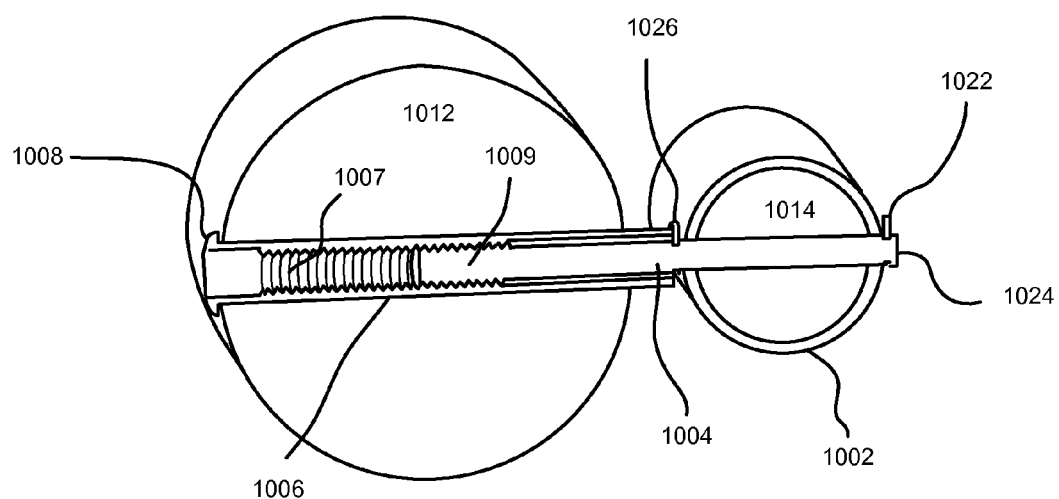
FIG. 11 is a cut-away view showing further details of an exemplary secondary anchor and connector component that may be used with a ring-shaped primary anchor of the invention.

In embodiments, the connector component 1004 and secondary anchor 1006 may provide for variable positioning and securing of the secondary anchor along the axial length of the connector component via a one-way ratcheting locking mechanism, a threaded engagement mechanism, or the like. For example, the outer surface of connector component 1004 may have a plurality of spaced protrusions such as angular teeth, ridges, barbs, detents, ribs, threads, or the like, which are adapted to be retained in a mating surface provided on the inside surface of the secondary anchor 1006. An example of such a configuration is shown in FIG. 11. Other configurations, such as those described above, including interference screws, etc., are also combinable with at least one ring-shaped anchor, such as primary anchor 1002. In alternative embodiments, the connector 1004 may be connected to the proximal portion of secondary anchor 1002, or may be disposed in a bore extending through bone 1014 and connected to the distal portion of the anchor 1002.

As shown in FIG. 11, secondary anchor 1006 may include a female threaded portion 1007 that engages with a male threaded portion 1009 of connector component 1004. By rotating, for example, connector component 1004, a desired spacing between the first metatarsal 1012 and the second metatarsal 1014 may be achieved. In order to place the structure shown in FIG. 11, a coaxial hole may be placed, for example, in the first and second metatarsals. A smaller diameter hole that starts at the medial side of the first metatarsal 1012 may be placed, extending through the second metatarsal 1014. The hole may then be enlarged in the first metatarsal 1012 to accommodate the larger diameter portion of the secondary anchor 1006. The connector component 1004 may then be slid into place, and a small incision used to provide access to add, for example, a retention clip 1022 on the outside of the second metatarsal 1014. The secondary anchor 1006 may then be inserted into the larger hole in the first metatarsal 1012 engaging the connector component 1004. The connector component 1004 and secondary anchor 1006 may be rotated to position the first metatarsal 1012 to the desired location.

Figure 12:
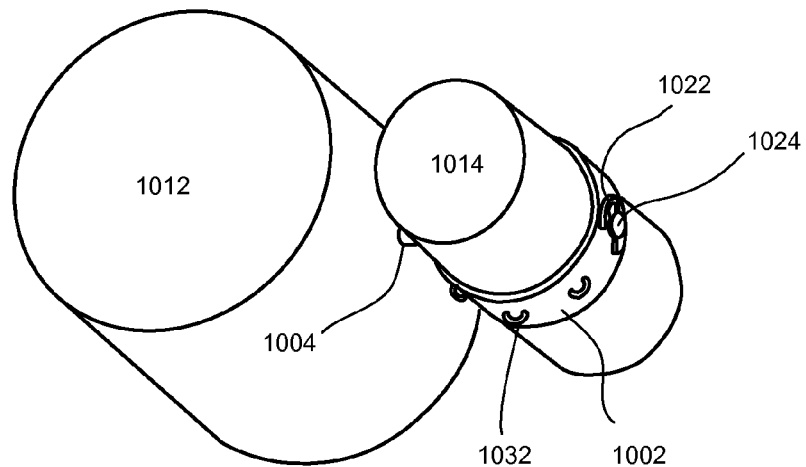
FIG. 12 is a schematic showing another embodiment of a primary ring-shaped anchor disposed around the outside of the bone having suture rings disposed thereon.

The combination of mating connectors may function to resist motion of the connector component 1004 in at least one direction. As shown in FIGS. 11 and 12, the mating connections may also include securing mechanisms, such as clips 1022, 1026, to secure the connector component in place with respect to the primary anchor. In addition, the arrangement of the anchors may be reversed so that the ring-shaped anchor 1002 is placed around the first metatarsal and the anchor 1006 is placed through the second metatarsal.

The connector component 1004 may include features for securing the connector component to an outer surface of the anchor 1002, such as holes, detents, grooves, rings, and the like. For example, as shown in FIG. 11, an annular channel may be provided around the distal end 1024 of the connector component 1004 to receive a securing clip, or the like. Additional channels may be included at other appropriate locations along the connector component 1004. For example, depending on an expected bone width, one or more annular channels may be included in the vicinity of clip 1026 to receive a securing clip and secure the connector component to the outer surface of anchor 1002 on each side of the second metatarsal 1014.

The connector component 1004 of system 1000 may be composed of suture material that may be elastic, braided, or monofilament in nature, or may be a wire, a polymeric strap, or any other suitable ratcheting material. As discussed herein, the connector component 1004 may be attached directly to one or both anchors or may be attached by an intermediate mechanism. The connection may be asymmetric to provide greater stiffness or flexibility in one direction over another.

The secondary anchor 1006 may be composed of a single body and may be secured into, for example, the first metatarsal using such means as screw threads, barbs, loops/cuffs, and the like to result in an interference fit. In an alternate embodiment, secondary anchor 1006 may be composed of a material that expands to lock the anchor in place.

Returning to FIG. 11, the secondary anchor 1006 may be adapted to have a slideable fit within the first metatarsal and/or may have an outer dimension that the allows the secondary anchor to act as a bushing to take up the space drilled in the first metatarsal or other bone. For example, secondary anchor 1006 may have a smooth outer surface like a washer or a bushing having dimensions selected to slide within the hole drilled in the first metatarsal. The secondary anchor 1006 may have a flange 1008, which abuts the proximal side of the first metatarsal thereby "sandwiching" the first metatarsal between the secondary anchor 1006 and the primary anchor 1002 fixed to the second metatarsal.

Alternatively, primary anchor 1002 and/or secondary anchor 1006 may be connected to a linkage to allow for a greater range of motion of the anchoring system, such as a ball joint and/or formed from a somewhat flexible material to form a lost motion connection. In other words, if the axial motion of the anchoring system is along the y-axis of connector component 1004, the linkage would permit motion along the x- or z-axis or a combination of x- and z-axes. For example, a ball joint or another type of lost-motion connection may be used to connect the primary anchor 1002 and the connector component 1004 and/or the connector component and the secondary anchor. This enables the relative position of the metatarsal to be adjusted in all three dimensions.

Figure 13:
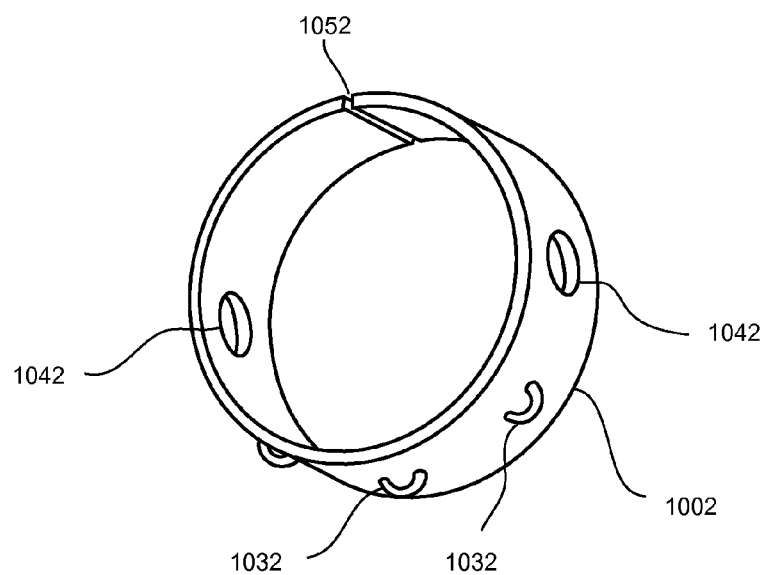
FIG. 13 is a schematic showing further details of the ring-shaped anchor of FIG. 12.

Referring to FIG. 13, additional details of the exemplary primary anchor of FIG. 12 are visible. As shown in FIG. 13, anchor 1002 may include suture rings 1032, axially aligned connector openings 1042, and/or a slot 1052. One or more connector openings 1042 may be used to allow a connector, such as connector component 1004 to pass through the anchor 1002. In embodiments, a single opening 1042 may be used to secure a connector component without the connector passing through the bone. For example, a connector opening 1042 may have a threaded portion, or the like, for securing to an end of a connector component, thereby securing the bone and the connector component via the ring anchor 1002.

Slot 1052, which may have a width considerably larger than illustrated, may be provided to allow for easy expansion and fitting of the anchor 1002 around the bone. In embodiments, the anchor 1002 may be made from a deformable material that can be closed around the bone, and/or the anchor 1002 may include a hinge (not shown) to assist in placement around a bone. In embodiments, the slot 1052 may be relatively larger than shown in FIG. 13, and, thus, anchor 1002 may wrap only partially around the bone. Suture rings 1032 may be provided to secure the anchor 1002 to the bone or other related anatomical structures, such as plantar tissue, that may be advantageously secured in proximity to the bone.

Figure 14:
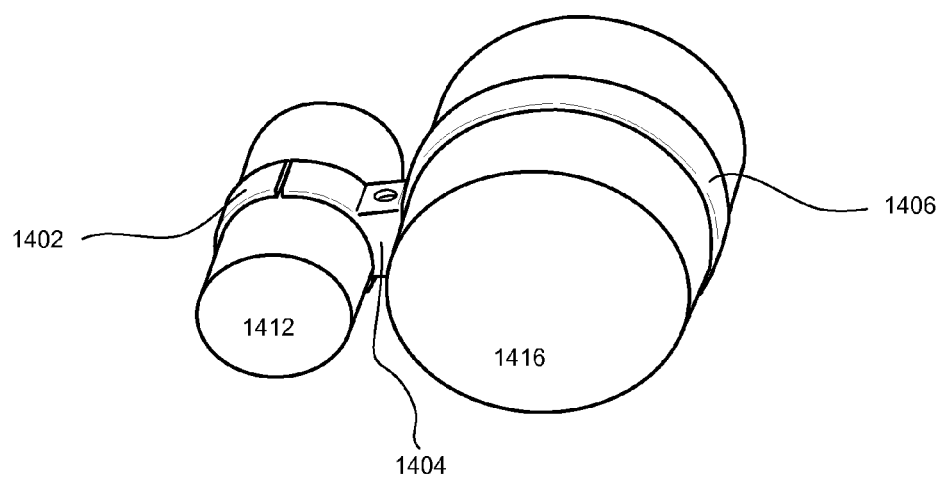
FIG. 14 is a schematic showing one embodiment of an anchoring system of the invention in which two ring-shaped anchors are disposed around the outsides of adjacent bones and separated by a spacer.

As shown in FIG. 14, other embodiments may also include anchors wrapping at least partially around two adjacent bones. For example, a primary anchor 1402 and a secondary anchor 1406 may be wrapped at least partially around second metatarsal 1412 and first metatarsal 1416, respectively. A connector component 1404 may be included to secure the anchors to one another, such as by a fixed spacer structure as shown in FIG. 14, or other configurations as described herein. In embodiments, a spacer component may be used as part of a connector component 1404 to achieve a desired separation distance between the bones. The spacer may be rigid or flexible as needed to accommodate a patient's prospective range of motion.

Figure 15:
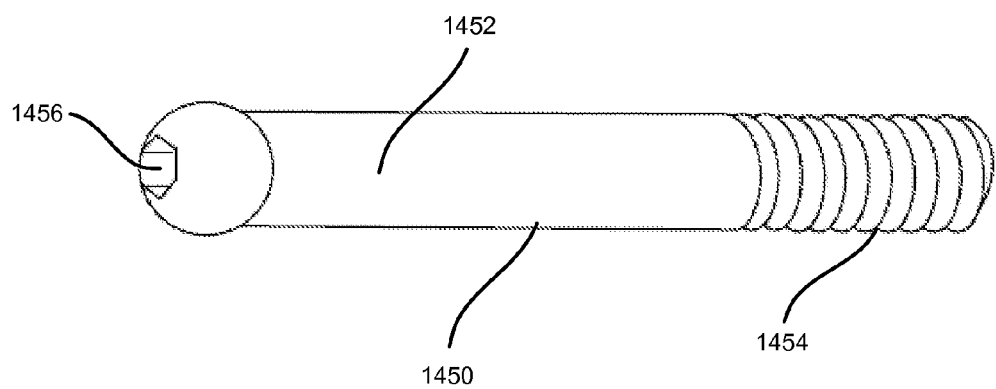
FIG. 15 is a schematic showing another embodiment of a connector having screw threads as a securing mechanism for primary or secondary anchors, and for positioning the anchors relative to each other.
Figure 16:
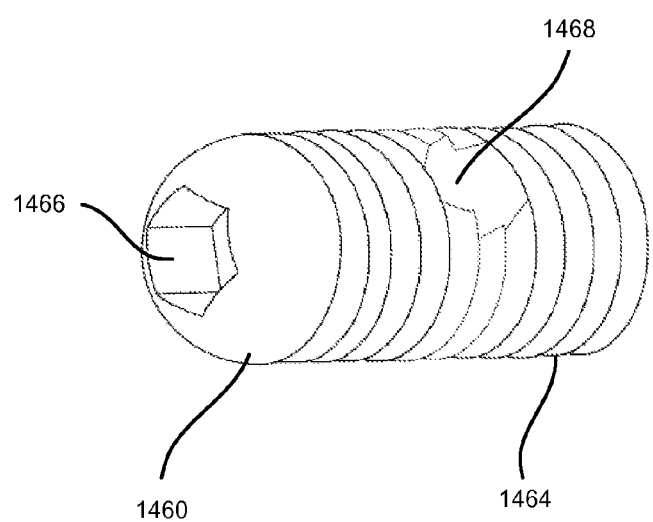
FIG. 16 is a schematic showing another embodiment of an implantable anchor of the invention having screw threads as an anchoring mechanism for use within a bone canal.
Figure 17:
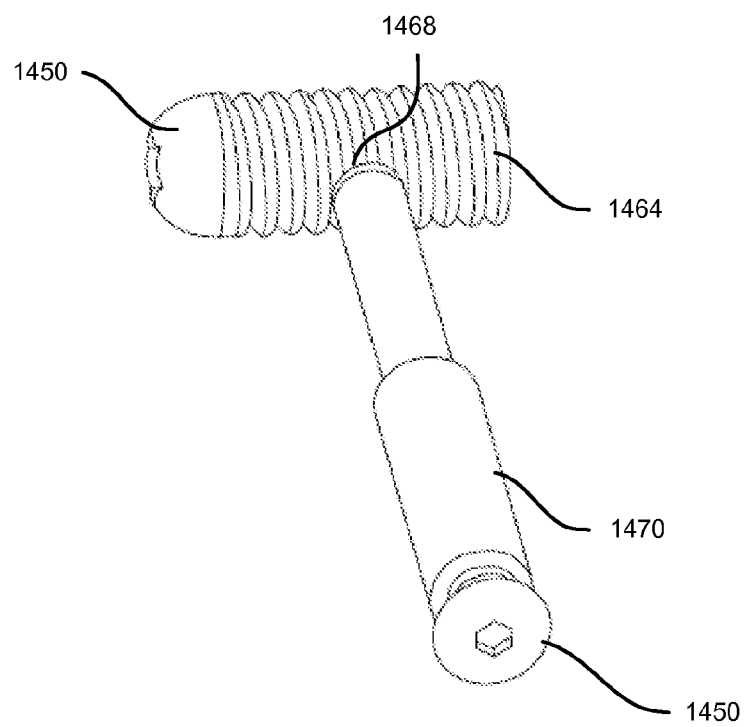
FIG. 17 is a schematic showing another embodiment of an anchoring system of the invention including the connector shown in FIG. 15 secured to the implantable anchor of FIG. 16.

FIGS. 15-17 illustrate yet another embodiment of the invention including a threaded connector and an implantable anchor. As shown in FIG. 15, connector 1450 may include a shaft 1452 with threads 1454 at one end, and socket 1456, or other adjustment means, at the other end. Connector 1450 may be constructed of various materials, and combinations of materials, as described herein, such as elastic, inelastic, bioabsorbable and non-bioabsorbable materials, and combinations thereof. Threads 1454 may be configured to engage with various implantable, through-bone, wrap-around, or partial wrap-around anchors described herein. Threads 1454 may be used as an adjustment mechanism to adjust a distance between first and second bones, e.g. by turning the shaft 1452 via socket 1456. In embodiments, connector 1450 may include threaded portions or other engagement and/or adjustment means described herein (e.g. angular teeth, ridges, barbs, detents, ribs, or the like) at both ends, or along the entire length, of the connector. Threads, or other engagement and/or adjustment means, at ends, or along the length, of the connector may be used to fixedly or adjustably secure the connector to opposing anchors, and/or spacers between the bones being treated. In the embodiment shown in FIG. 15, the end of the connector including socket 1456 includes an enlarged flange, that may act as an anchor to prevent the connector 1450 from passing through one of the bones being treated, or passing through a wrap-around or partial wrap-around anchor. FIG. 16 depicts an implantable anchor 1460 that may be used with connector 1450.

As shown in FIG. 16, implantable anchor 1460 may include threads 1464 and a socket 1466. Anchor 1460 may be sized and configured for insertion to an intramedullary canal, such as in the metatarsal. Threads 1464 may secure the anchor 1460 in the intramedullary canal and axial adjustment of the anchor may be accomplished by turning the anchor via socket 1466. Anchor 1460 may also include one or more cavities 1468 configured to engage with, for example, the threads 1454 of connector 1450, or other engagement and/or adjustment means described herein. An example of a combined configuration of anchor 1460 and connector 1450 is shown in FIG. 17.

As shown in FIG. 17, anchor 1450 may be implanted axially in a bone canal of a first bone (not shown) and connector 1450 screwed into cavity 1468. Connector 1450 may be inserted through a pilot hole in the side of the first bone to reach anchor 1450. As with other connectors described herein, connector 1450 may pass through a second bone (not shown), and optionally through a through-bone, wrap-around, or partial wrap-around anchor attached to the second bone. For example, barrel 1470, which may be configured as a through-bone anchor or adjustment mechanism, may be disposed in a tunnel drilled through the second bone, and may include threads, or other engagement mechanisms, to fixedly or adjustably secure the connector 1450 to the barrel 1470. It should be noted that, when used as a through-bone anchor, barrel 1470 may optionally include various combinations of the features described herein for securing the barrel as an anchor in the second bone. Connector 1450 may also include other adjusting mechanisms, such as multiple threaded segments that adjust with respect to each other when rotation of one segments is inhibited or prevented. For example, connector 1450 may include two or more physically separated pieces with male threaded segments, and barrel 1470 may include internal female threads that engage with the male threads of at least one of the separate connector segments. The barrel 1470 may optionally be fixed to, or integrally formed with, one of the connector segments, or may include threaded engagements at both ends. Thus, the length of the overall connector 1450 may be expanded, or reduced, when rotation of the threaded end 1454 is inhibited, or prevented, by at least one male threaded segment moving with respect to the female threaded barrel 1470. The above adjustment mechanisms and thread arrangements are merely exemplary, and various configurations falling within the scope of the invention will be appreciated by those of skill in the art upon understanding the concepts described herein.

Figure 18:
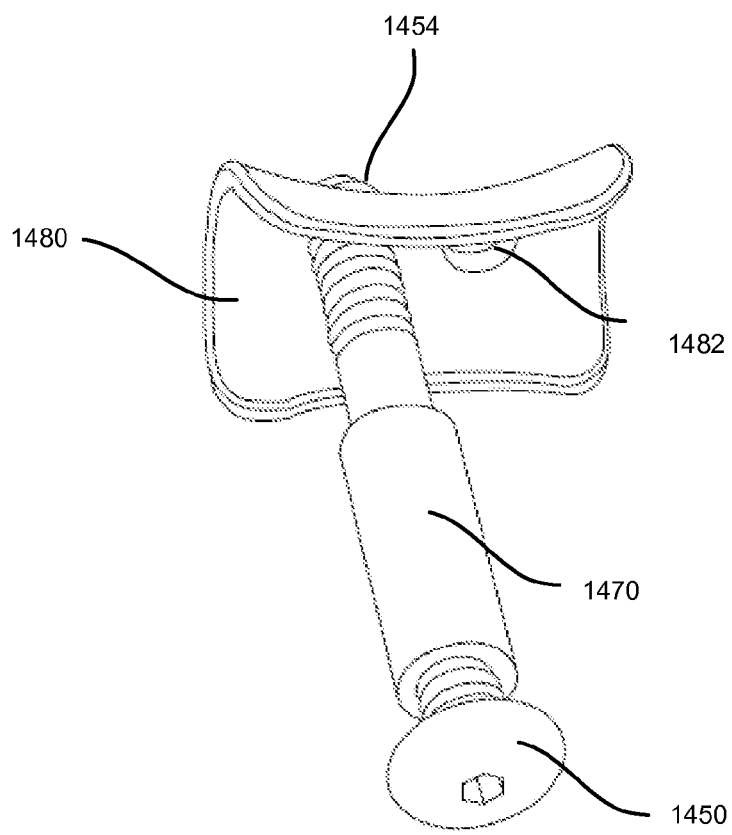
FIG. 18 is a schematic showing another embodiment of an anchoring system of the invention including an anchor that is contoured to fit around a metatarsal, and a connector that is secured to the anchor by a threaded engagement.

FIG. 18 illustrates yet another embodiment of the invention that may include a connector as described above with reference to FIGS. 15 and 17, along with a partial wrap-around anchor, which may take the form of a saddle. As shown in FIG. 18, anchor 1480 wraps partially around one of the bones being treated, e.g. a first or second metatarsal. Anchor 1480 may include one or more partial cavities or through-holes, such as through-holes 1482, for receiving an end of a connector, such as connector 1450, or the like. Through-holes, such as through-holes 1482, may include female threads, or other engagement means, to fixedly or adjustably secure the connector 1450 to the anchor 1480. However, in some embodiments, holes in the anchor 1480 may be relatively smooth, and not include engagement means. For example, connectors, such as connector 1450, may be prevented from passing through anchor 1480 by a flange included at the end of the connector, a detent and clip configuration, etc. In such cases, adjustment of a spacing between the bones may be provided by screwing the connector 1450 into the barrel 1470, or other adjustment means, thereby pulling the bones together.

Figure 19:
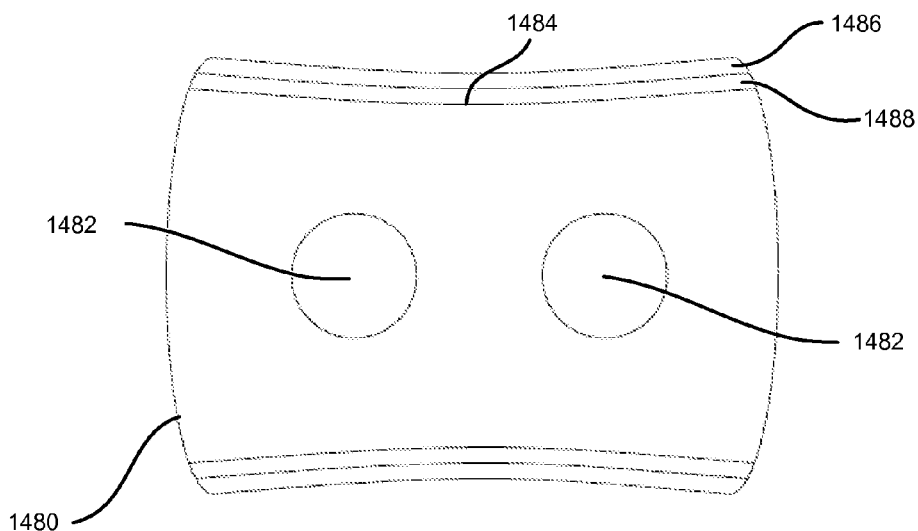
FIGS. 19 and 20 are schematic side and front elevation views showing further details of the anchor shown in FIG. 18, including dorsal and plantar extensions.
Figure 20:
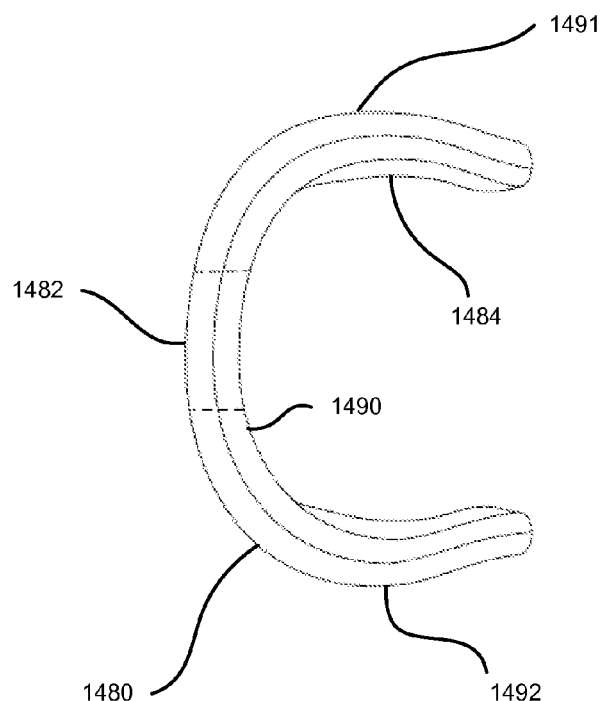

Anchor 1480 may be configured to fit closely with a particular bone such as a first or second metatarsal. In embodiments, either, or both, of a primary anchor and a secondary anchor such as anchor 1480, may be contoured to an anatomical shape of a bone to be treated, e.g. a metatarsal, phalanx, etc. Such contours may include developable and/or non-developable surfaces. Developable surfaces may include, for example, cylindrical or conical shapes, whereas non-developable surfaces include Gaussian curvature, e.g. partial spheroids, three-dimensional saddles, depressions, etc. In embodiments, a preformed contour of at least one of the primary anchor and the secondary anchor may include a saddle, or depression, that substantially matches an anatomical shape of the bone to be treated, e.g. a metatarsal (such as shown in FIGS. 3, 5 and 8), or phalanx. FIGS. 19 and 20 show a three-dimensional saddle form of anchor 1480 in more detail. Saddle 1484 is provided that includes both a cylindrical curvature around the bone to be treated and a depression around the circumference of the bone, which may be preferable for fitting around a metatarsal such as shown in FIG. 8. Such three-dimensional curves may be beneficial in closely fitting the anchor to the bone and evenly distributing forces across the bone surface, as well as helping to prevent axial displacement of the anchor or associated tissue after being secured to the bone.

Although FIG. 18 shows a single anchor 1480 as might be disposed on a first bone, it should be appreciated that a similar anchor may be included on an opposite bone to be treated. For example, the connector 1456 may pass through and abut one partial wrap-around anchor on the first metatarsal, pass through the first metatarsal, pass through the second metatarsal, and pass through and engage with another partial wrap-around anchor on the opposite side of the second metatarsal. Additional details of exemplary partial wrap-around anchor 1480 are shown in FIGS. 19 and 20.

As shown in FIG. 19, the wall of the anchor 1480 may include a plurality of (in this case two) cavities or through-holes 1482 to receive and/or engage with the connector(s). Thus, according to embodiments, either, or both, of the primary anchor and the secondary anchor may be adapted to be secured to a plurality of connectors, e.g. secured to two connectors disposed diagonally, crossing or parallel to one another. In embodiments, one or more partial cavities (i.e. cavities that do not form through-holes), or perforations such as through-holes 1482, of the primary and/or secondary anchor(s), may be threaded for fixedly, or adjustably, securing the connector(s) to the primary or secondary anchor. By way of further example, if partial cavities are used, instead of through-holes, the connector may be securely seated in the anchor by bottoming out a fastener, such as a bolt, in the partial cavity. In such cases, adjustment of a distance between bones may be achieved by adjusting the relative distance of the other anchor, e.g. by screwing the connector 1450 into barrel 1470, by a ratcheted connector end, etc.

As also shown in FIG. 19, anchor 1480 may be constructed from layers 1486, 1488 of different material, depending on intended usage. For example, a first layer 1486 may be comprised of a relatively rigid material that is effective for distributing the tensile force from the connector across a surface of the bone, and also for assuming and/or maintaining a desired shape, e.g. an anatomical shape of the bone to be treated. Such materials may be, for example, thermosetting or thermoplastic polymers or other materials. A second layer 1488 may be comprised of a material that is particularly suited for contact with the bone to be treated and may include, for example, substances such as those described herein intended to promote (or retard) bone growth or adhesion may be used in layer 1488 depending on whether the anchor 1480 is intended to be left in place, bioabsorbed or removed.

As shown in FIG. 20, anchor 1480 may have a base portion 1490 configured to extend axially along a length of the bone, and one or more flanges, such as dorsal and plantar extensions 1491, 1492, attached to the base portion 1490. Flanges, such as dorsal extension 1491 and/or plantar extension 1492, may extend generally transversally from base portion 1490, or at other angles depending on intended usage, and may be adjustable, such as by using a deformable material, hinges, etc. Dorsal and plantar extensions 1491, 1492 may be configured to wrap partially around the bone and/or associated tissue. Such extensions may be used, for example, to provide additional security to the bone fixation, and may also be used to hold tissue, such as the plantar plate, in position after reconstruction and/or repair of an affected joint.

Figure 21:
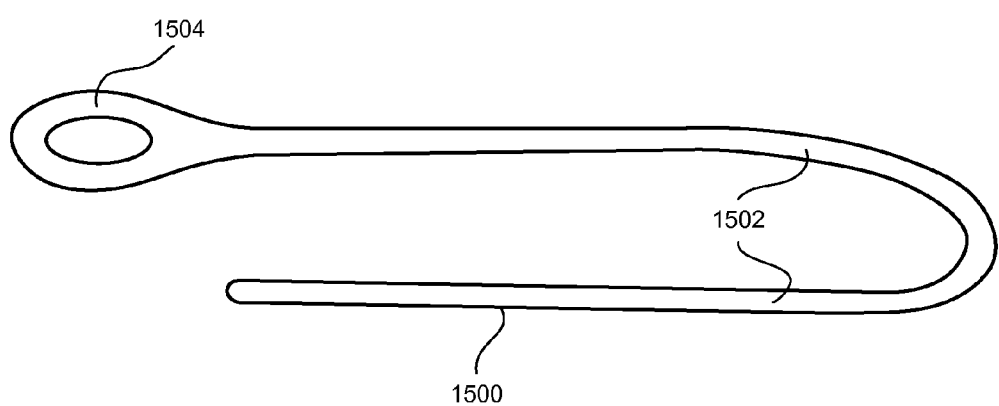
FIG. 21 is a schematic showing another embodiment of an anchor that may be looped around the outside of a bone.

FIGS. 21-24 illustrate yet another embodiment of the invention where a connector and looped anchor may be combined. As shown in FIG. 21, a wrap-around anchor 1500 may include an elongate portion 1502 and a loop 1504 at an end. Wrap-around anchor 1500 may comprise multiple joined elements, or may be a substantially unitary construction. For example, a unitary wrap-around anchor 1500 may be manufactured using a flexible material, e.g. suture, tape, elastic, biomaterial, etc., and may be manufactured so that one end of the material has a closed loop and the other a free end. The elongate portion 1502 may be manufactured using an elastic or inelastic material, including various materials described herein, depending on intended usage.

Alternatively, the loop end of the wrap-around anchor 1500 may be fabricated from a relatively flexible material such as those mentioned above, e.g. to enhance the ability to wrap around and conform to an outer bone surface, and at least a portion of the elongate portion 1502 may be fabricated from a relatively rigid material, e.g. to enhance stability of the bridge formed by the anchor when securing two bones. Further details regarding an exemplary employment of the wrap-around anchor 1500 are shown in FIGS. 22-24.

Figure 22:
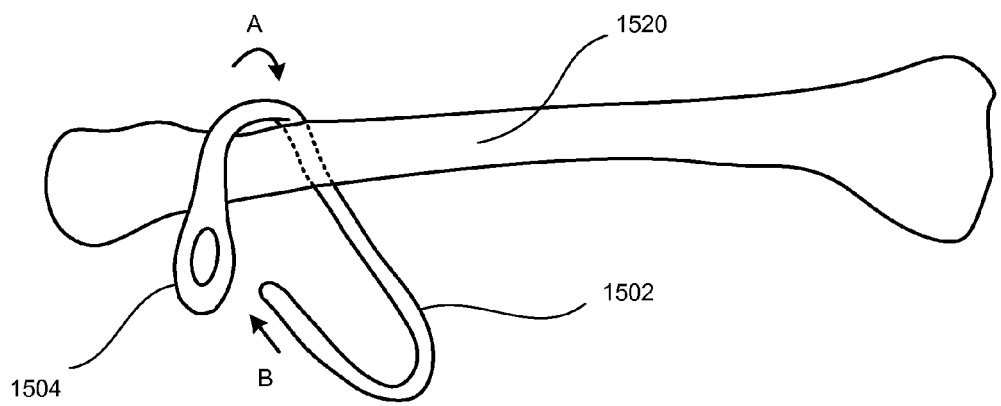
FIG. 22 is a schematic showing the anchor of FIG. 21 being looped around a bone.

Beginning with FIG. 22, the wrap-around anchor may be routed around a bone 1520, such as a second metatarsal, in the direction indicated by arrow "A." A free end of the elongate portion 1502 may then be directed toward the loop 1504 as indicated by arrow "B."

Figure 23:
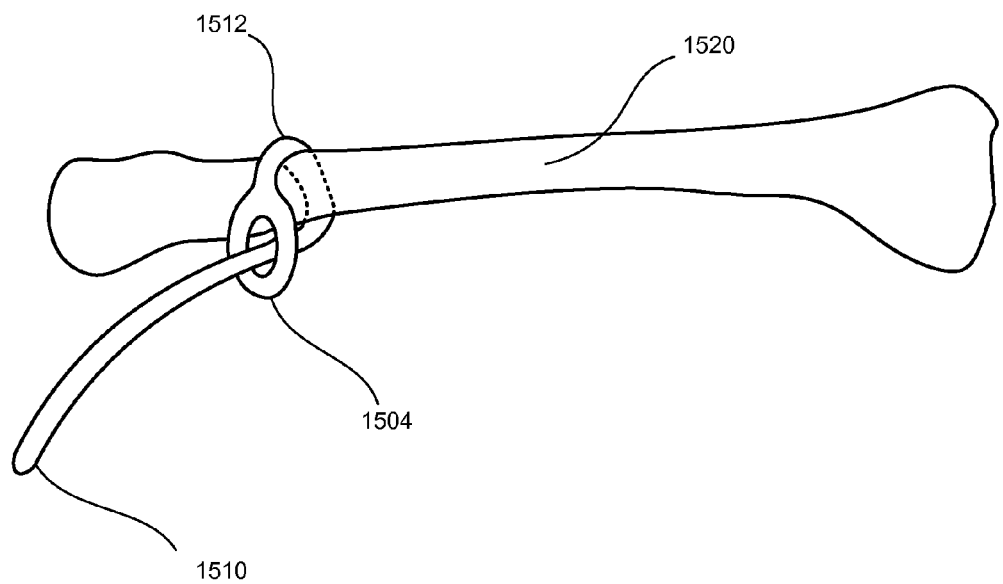
FIG. 23 is a schematic showing the anchor of FIG. 22 being secured to a bone.
Figure 24:
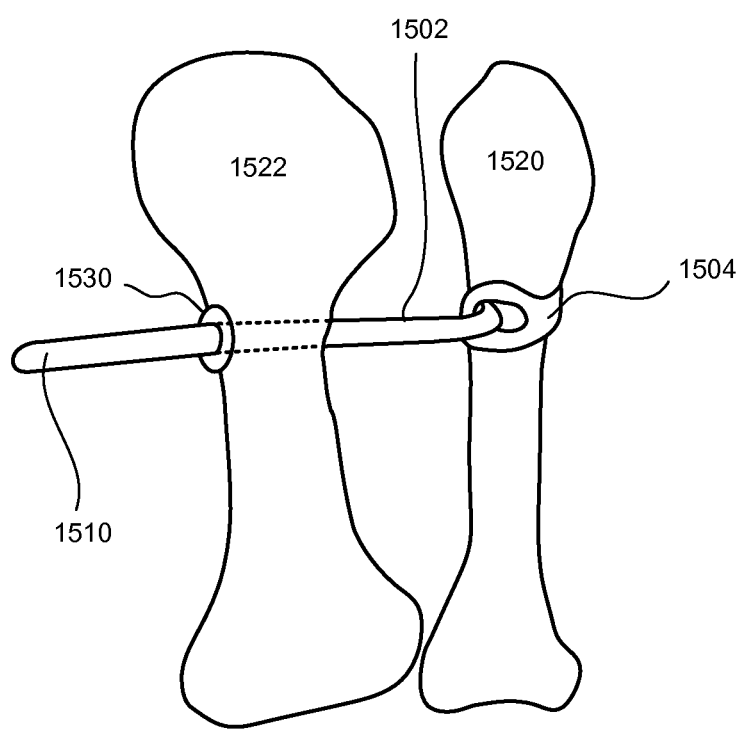
FIG. 24 is a schematic showing the anchor of FIG. 23 looped around a first bone, and anchored through a second bone.

As shown in FIG. 23, the free end 1510 may be pulled through the loop 1504, and tension applied to conform a portion 1512 of the wrap-around anchor to the bone 1520. As noted previously, at least part of the elongate portion 1502 of the wrap-around anchor may be relatively flexible to promote a conformal or nearly conformal fit between the wrap-around anchor 1500 and the bone 1520. The free end of the wrap-around anchor 1500 may then be secured to, or through, another bone. One example of such securing is shown in FIG. 24.

The wrap-around anchor 1500 may be configured to engage with various secondary anchors such as those discussed herein. For example, as shown in FIG. 24, the free end 1510 may be fed through an anchor in and/or on bone 1522 and secured to the bone 1522 with an anchor ring or other closure 1530. In embodiments, bone 1522 may be a first metatarsal, bone 1520 may be a second metatarsal, and the wrap-around anchor 1500 may be used as part of an anchor system to secure the first metatarsal to the second metatarsal, e.g. to reduce the intermetatarsal (IM) angle.

Figure 25A:
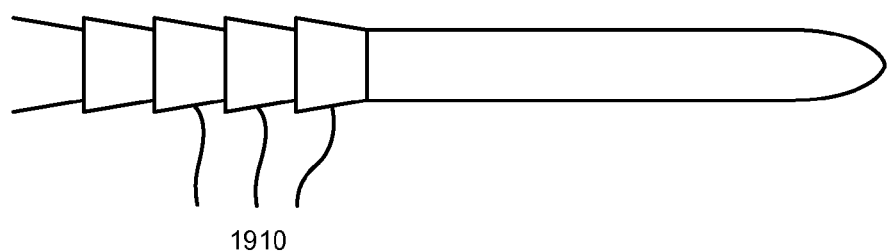
FIGS. 25A-25C are schematics showing various engagement mechanisms that may be applied to an anchor such as shown in FIGS. 21-24.
Figure 25B:
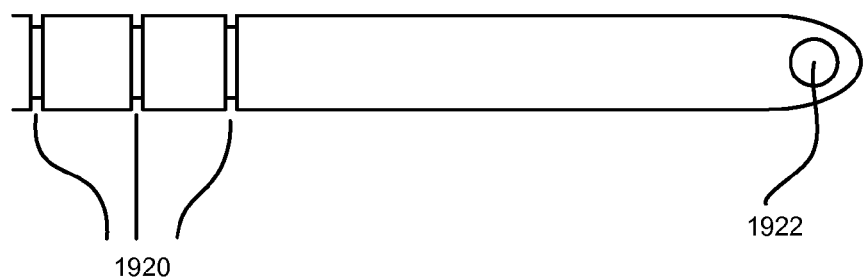
Figure 25C:
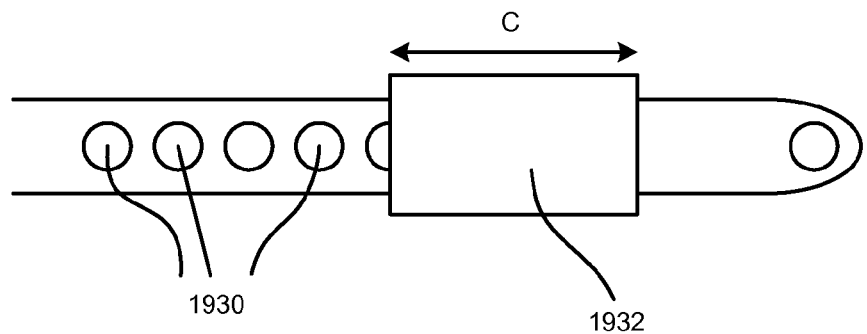

In embodiments, at least part of the elongate portion 1502 may provide for variable positioning and securing of the wrap-around anchor 1500 along an axial length of the elongate portion 1502, e.g. via a one-way ratcheting locking mechanism, detents, anchor holes, or the like. Some examples of such configurations are shown in FIGS. 25A-25C. For example, the outer surface of a portion of the elongate portion 1502 may have a plurality of spaced protrusions such as angular teeth (e.g. teeth 1910), ridges, barbs, detents (e.g. detents formed by recesses 1920), ribs, threads, or the like, which are adapted to be retained in a mating surface provided on the inside surface of, or an opposite side of, a secondary anchor such as those described herein. The free end of the wrap-around anchor 1500 may also include features for assisting with pulling tension, such as an eyehole 1922 as shown in FIG. 25B, or other positive engagement mechanism.

As shown in FIG. 24, the relative position of the bones 1520 and 1522 may be adjusted by pulling on the free end 1510 to move the elongate portion 1502 relative to anchor ring 1530, or other secondary anchor, and secured in place via a locking/ratcheting mechanism, such as those described herein, or others known in the art. This adjustment may be accomplished by a variety of mechanical means including winding the elongate portion 1502 onto a screw or using a lever for tension. The locking/ratcheting may be automatic or may be actuated by the user. The locking/ratcheting may be permanent or allow for future adjustment.

As noted above, an anchor ring 1530, or other closure, may be provided to secure the wrap-around anchor 1500 at a desired length on an opposite side of, or in, bone 1522. For example, anchor ring 1530 may include a C clip that is configured to secure in a detent similar to those shown in FIG. 25B. It will be appreciated that, as described throughout the specification, the secondary anchoring mechanism on, and/or in, the bone 1522 may take many forms without departing from the scope of the invention. Anchor ring 1530 may be substituted, for example, by a pin that pierces the elongate portion 1502 at any desired length, or that is sized to be placed through one or more anchor holes provided along an axial length of the elongate portion 1502, such as anchor holes 1930 shown in FIG. 25C. Thus, after passing through the loop 1504, the free end 1510 of the wrap-around anchor 1500 may be brought through a drill hole in the bone 1522, or through an in-bone anchor as previously described herein, and secured on an opposite side of, or in, bone 1522. Excess portions of the elongate portion 1502 may be removed after permanently or temporarily fixing the wrap-around anchor 1500 at the desired length.

In embodiments, the free end 1510 of the wrap-around anchor 1500 may be fed through a spacer component, such as annular spacer 1932 schematically shown in FIG. 25C. Preferably, this may be done after the free end 1510 is passed though the loop 1505, e.g. allowing the spacer to have a diameter greater than a diameter of the loop. A spacer may be used as part of an anchor system including wrap-around anchor 1500, for example, to achieve a desired fixed separation distance between the bones and/or provide additional rigidity to the elongate portion of the wrap-around anchor 1500. The spacer may be rigid or flexible as needed to accommodate a patient's prospective range of motion. In embodiments, the spacer, such as spacer 1932, may be axially moveable along the elongate portion 1502, i.e. in direction "C" shown in FIG. 25C, and/or may have a length corresponding to a desired distance between the bones. In embodiments, the spacer may be manufactured from a compressible and/or elastic material, or otherwise configured to provide compression and/or extension, to allow for a desired range of motion.

According to another feature of the invention, bony healing may be induced during the surgical procedure of the invention by introducing bone growth factors such as bone morphogenetic proteins (BMPs) and basic fibroblast growth factor (bFGF) to the target area undergoing correction. These two classes of bone growth factors have been shown to accelerate bone regeneration, bone healing to prosthetic-like implants, and increase strength and stability to the bony callus. The bone growth factors could be delivered to the target area by a variety of methods. One method may be to introduce the bone growth factors in combination with a collagen matrix, which could be a gel- or sponge-like material, to the target area. The bone growth factor may then stimulate the patient's own bone cells into action, while the collagen may provide the scaffolding into which the stimulated bone cells can grow. In the end, bone could replace the collagen scaffold, which may be eventually resorbed.

Another method of delivery may be to coat the anchor screws or interference screws with the bone growth factor in combination with hydroxyapatite, which may have a synergic stimulative effect on the bone cells. For this to be accomplished, an effective amount of the bone growth factor would be absorbed to a gritblasted hydroxyapatite coated anchor or screw prior to implantation into the bone.

However, an alternate method to the delivery of recombinant bone growth factors may be through gene therapy. Delivery by gene therapy may be more cost effective because ex vivo production of DNA for clinical use is inexpensive compared with traditional methods of protein production. Also, gene therapy may be a more efficient way to deliver the bone growth factors compared with traditional protein delivery. One desirable way to utilize gene therapy in the surgical procedure of the invention may be to introduce plasmid-encoded proteins capable of inducing bone growth to the area of distraction. This may be accomplished by introducing biodegradable matrices, such as collagen sponges, containing expression plasmid DNA encoding bone growth factors, also known as gene-activated matrices (GAMs), to the target area.

The description and examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the medical sciences, orthopedic surgery, or related fields are intended to be within the scope of the appended claims.

The disclosures of all references and publications cited above are expressly incorporated by reference in their entireties to the same extent as if each were incorporated by reference individually.

What is claimed is:

1. A surgical method for repair of a foot affected with hallux valgus with a surgical kit comprising a first anchor, a second anchor and a connector, said method comprising the steps of:
    creating a tunnel across a second metatarsal;
    securing the first anchor to the second metatarsal of the foot including placing the first anchor at least partially around the second metatarsal;
    inserting the connector through the tunnel;
    securing the second anchor to a first metatarsal of the foot; and
    connecting the first and second anchors to one another with the connector;
    wherein at least the first anchor comprises an inner surface having a cross section that is concave and is secured to the second metatarsal by placing the inner surface about an outer surface of the second metatarsal,
    wherein the first anchor comprises a first portion and a second portion, wherein the first anchor is placed about the second metatarsal so that the first portion and second portion are located on opposite sides of the second metatarsal.

2. The method of claim 1, further comprising:
    entering tissues of the foot affected with hallux valgus by performing at least one incision;
    performing a soft-tissue release to release an abductor tendon, fibular sesamoid attachments and a lateral metatarsophalangeal (MTP) joint capsule of the foot;
    shaving an exostosis of the foot;
    wherein the at least one incision comprises one of i) a medial incision at the first metatarsal; ii) a lateral incision to the second metatarsal at its distal portion; and iii) a first web space incision.

3. The method of claim 1, further comprising the steps of:
    inserting the connector through the first anchor;
    securing the connector to the first anchor; and
    securing the connector to the second anchor.

4. The method of claim 3, further comprising attaching a clip to a portion of the connector that substantially prevents the connector from pulling back through the first anchor.

5. The method of claim 1, further comprising adjustably engaging a portion of the connector with an interior surface of the first anchor.

6. The method of claim 1, further comprising adjustably engaging a threaded portion of the connector with a threaded interior surface of the first anchor.

7. The method of claim 1, wherein the first anchor includes at least one suture receiving portion, the method further comprising suturing at least one of a tendon, ligament, and a plantar plate to the suture receiving portion.

8. The method of claim 1, wherein the first anchor has a Gaussian curvature shape.

9. The method of claim 1, wherein the inner surface of the first anchor substantially conforms to a shape of the second metatarsal on which the inner surface is placed.

10. The method of claim 1, wherein the inner surface of the first anchor has a cylindrical curvature.

11. The method of claim 1, wherein the first anchor has a "C" shaped cross section.

12. The method of claim 11, wherein the inner surface of the first anchor substantially conforms to a shape of the second metatarsal on which the inner surface is placed.

13. The method of claim 1, further comprising adjusting a distance between the first and second metatarsals.

14. The method of claim 13, wherein the connector comprises an adjustment mechanism and the method further comprises adjusting the distance between the first and second metatarsals with the adjustment mechanism.

15. The method of claim 1, the first anchor is secured to the second metatarsal to prevent displacement of tissue.

16. The method of claim 1, wherein the first anchor wraps at least partially around the second metatarsal and associated tissue of the foot to hold the tissue in position.

17. The method of claim 1, wherein the first anchor wraps at least partially around the second metatarsal to hold a plantar plate tissue of the foot in position.

18. The method of claim 1, further comprising adjusting, with the surgical kit, an intermetatarsal angle between the first metatarsal and the second metatarsal.

19. The method of claim 1, further comprising, with the surgical kit:
 adjusting an intermetatarsal angle between the first metatarsal and the second metatarsal; and
 adjusting a hallux valgus angle between the first metatarsal and a proximal phalanx of the foot.

20. The method of claim 19, wherein the method further comprises placing the first anchor at least partially around the second metatarsal and associated tissue of the foot to hold the tissue in position.

21. The method of claim 1, wherein the first anchor is rigid.

22. The method of claim 1, wherein the first portion and the second portion extend in the same direction with respect to the cross section of the inner surface of the first anchor.

* * * * *